US010512672B2

(12) United States Patent
Chavez et al.

(10) Patent No.: US 10,512,672 B2
(45) Date of Patent: Dec. 24, 2019

(54) METHODS FOR THE TREATMENT OF INFLAMMATORY JOINT DISEASE

(71) Applicants: Xalud Therapeutics, Inc., Oakland, CA (US); The Regents of the University of Colorado, a Body Corporate, Denver, CO (US)

(72) Inventors: Raymond A. Chavez, San Francisco, CA (US); Linda R. Watkins, Boulder, CA (US); Robert Landry, Erie, CO (US)

(73) Assignees: Xalud Therapeutics, Inc., Berkeley, CA (US); The Regents of the University of Colorado, a Body Corporate, Denver, CO (US)

(*) Notice: Subject to any disclaimer, the term of this patent is extended or adjusted under 35 U.S.C. 154(b) by 34 days.

(21) Appl. No.: 14/905,915

(22) PCT Filed: Jul. 17, 2014

(86) PCT No.: PCT/US2014/047071
§ 371 (c)(1),
(2) Date: Jan. 18, 2016

(87) PCT Pub. No.: WO2015/009955
PCT Pub. Date: Jan. 22, 2015

(65) Prior Publication Data
US 2016/0235816 A1 Aug. 18, 2016

Related U.S. Application Data

(60) Provisional application No. 61/847,851, filed on Jul. 18, 2013.

(51) Int. Cl.
*A61K 38/20* (2006.01)
*A61K 48/00* (2006.01)
*C07K 14/54* (2006.01)

(52) U.S. Cl.
CPC ........ *A61K 38/2066* (2013.01); *A61K 48/005* (2013.01); *A61K 48/0075* (2013.01); *A61K 48/0091* (2013.01); *C07K 14/5428* (2013.01)

(58) Field of Classification Search
None
See application file for complete search history.

(56) References Cited

U.S. PATENT DOCUMENTS

| | | |
|---|---|---|
| 5,231,012 A | 7/1993 | Mosmann et al. |
| 5,373,317 A | 12/1994 | Salvati et al. |
| 5,716,804 A | 2/1998 | Moore et al. |
| 5,783,567 A | 7/1998 | Headley |
| 5,922,018 A | 7/1999 | Sarvazyan |
| 6,018,036 A | 1/2000 | Mosmann et al. |
| 6,083,919 A | 7/2000 | Johnson et al. |
| 6,159,937 A | 12/2000 | Larsen et al. |
| 6,165,754 A | 12/2000 | Crystal et al. |
| 6,201,880 B1 | 3/2001 | Elbaum et al. |
| 6,217,857 B1 | 4/2001 | Mosmann et al. |
| 6,403,077 B1 | 6/2002 | Strom et al. |
| 6,413,942 B1 | 7/2002 | Felgner et al. |
| 6,428,985 B1 | 8/2002 | Bromberg et al. |
| 6,652,850 B1 | 11/2003 | Philip et al. |
| 6,875,748 B2 | 4/2005 | Manthrope et al. |
| 7,261,882 B2 | 8/2007 | Watkins et al. |
| 7,749,490 B2 | 7/2010 | Sommer et al. |
| 7,846,428 B2 | 12/2010 | Fisher |
| 7,897,380 B2 | 3/2011 | Kay et al. |
| 8,524,678 B2 | 9/2013 | Watkins et al. |
| 8,598,133 B2 | 12/2013 | Rothblum Watkins et al. |
| 2003/0044384 A1 | 3/2003 | Roberts et al. |
| 2003/0049256 A1 | 3/2003 | Tobinick |
| 2003/0130221 A1 | 7/2003 | High et al. |
| 2003/0147855 A1 | 8/2003 | Zolotukhin et al. |
| 2003/0166593 A1 | 9/2003 | Chien et al. |
| 2003/0232781 A1 | 12/2003 | Wolffe et al. |
| 2004/0115277 A1* | 6/2004 | Kissel .................. A61K 9/1647 424/489 |
| 2004/0142893 A1 | 7/2004 | Ikeda et al. |

(Continued)

FOREIGN PATENT DOCUMENTS

| | | |
|---|---|---|
| EP | 1287781 A1 | 3/2003 |
| JP | 2003-146909 A | 5/2003 |

(Continued)

OTHER PUBLICATIONS

Barman, et al., "Two methods for quantifying DNA extracted from poly(lactide-co-glycolide) microspheres", J. of Controlled Release, 69:337-44 (2000).

Bennet, et al., "Preclinical Models of Neurologic and Psychiatric Disorders", in Current Protocols in Neuroscience (2003), C/R John Wiley & Sons, Inc., p. 9.14.1-9.14.16.

Cohen, et al., Controlled Delivery Systems for Proteins Based on Poly(Lactic/Glycolic Acid) Microspheres, Pharmaceutical Res., 8(6):713-20 (1991).

Hartmann, et al., "The AMPA Receptor Subunites GluR-! and GluR-B Reciprocally Modulate Spinal Synaptic Plasticity and Inflammatory Pain", Neuron, 44:637-50 (2004).

Kontinen and Meert, "Predictire Validity of Neuropathic Pain Models in Pharmacological Studies with a Behavioral Outcome in the Rat: A Systmatic Review", Proceedings of the 10th World Congress on Pain, Chapter 40, pp. 480-498 (2003).

(Continued)

*Primary Examiner* — Addison D Ault
(74) *Attorney, Agent, or Firm* — Wolf, Greenfield & Sacks, P.C.

(57) ABSTRACT

This invention provides compositions and methods for preventing inflammatory diseases of the joints, including rheumatoid and osteoarthritis, tendonitis, bursitis, inflammation of the ligament, synovitis, gout, and systemic lupus erythematosus, wherein the methods include injecting into the inflamed joint a therapeutic anti-inflammatory composition comprising a bacterial or viral IL-10 expression construct, wherein the IL-10 expression construct comprises a bacterial or viral backbone and a nucleic acid sequence encoding interleukin-10.

36 Claims, 5 Drawing Sheets

(56) References Cited

U.S. PATENT DOCUMENTS

| | | | |
|---|---|---|---|
| 2004/0241141 A1* | 12/2004 | Pawliuk | A61K 38/1709 |
| | | | 424/93.2 |
| 2004/0258671 A1 | 12/2004 | Watkins | |
| 2005/0129669 A1 | 6/2005 | Treco et al. | |
| 2005/0203032 A1 | 9/2005 | Yang et al. | |
| 2006/0073119 A1 | 4/2006 | Forsayeth et al. | |
| 2006/0088909 A1* | 4/2006 | Compans | C07K 14/005 |
| | | | 435/69.1 |
| 2006/0116321 A1 | 6/2006 | Robbins et al. | |
| 2007/0003518 A1 | 1/2007 | Atkinson et al. | |
| 2008/0274202 A1 | 11/2008 | Kraig et al. | |
| 2009/0035256 A1* | 2/2009 | Sommer | C07K 14/5428 |
| | | | 424/85.2 |
| 2009/0136453 A1 | 5/2009 | Watkins et al. | |
| 2009/0208563 A1 | 8/2009 | Watkins et al. | |
| 2010/0028296 A1 | 2/2010 | Chavez et al. | |
| 2010/0196492 A1 | 8/2010 | Green et al. | |
| 2012/0058102 A1 | 3/2012 | Wilson et al. | |
| 2013/0172410 A1 | 7/2013 | St. Laurent | |
| 2013/0337556 A1 | 12/2013 | Watkins et al. | |
| 2014/0093476 A1 | 4/2014 | Watkins et al. | |
| 2015/0044281 A1 | 2/2015 | Watkins et al. | |
| 2019/0112354 A1 | 4/2019 | Forsayeth et al. | |

FOREIGN PATENT DOCUMENTS

| | | |
|---|---|---|
| JP | 2004-515527 | 5/2004 |
| JP | 2008-541759 | 11/2008 |
| WO | WO 94/004180 A2 | 3/1994 |
| WO | WO 98/024469 A1 | 6/1998 |
| WO | WO 99/008702 A1 | 2/1999 |
| WO | WO 99/047157 A1 | 9/1999 |
| WO | WO 99/056784 A2 | 11/1999 |
| WO | WO 02/047664 A2 | 6/2002 |
| WO | WO 2003/102237 A1 | 12/2003 |
| WO | WO 2004/017831 A1 | 3/2004 |
| WO | WO/US 2005/000215 | 1/2005 |
| WO | WO 2005/018440 A1 | 3/2005 |
| WO | WO/US2006/130580 | 5/2006 |
| WO | WO/US 2006/119170 | 11/2006 |
| WO | WO/US 2006/130581 | 12/2006 |
| WO | WO/US2013/103966 | 7/2013 |
| WO | WO 2015/009955 A1 | 1/2015 |

OTHER PUBLICATIONS

Ledeboer, et al., "Regional and temporal expression patterns of interleukin-10, interleukin-10 receptor and adhesion molecules in the rat spinal cord during chronic relapsing EAE", J. of Neuroimmunology, 136:94-103 (2003).

Makadia and Siegel, "Poly Lactic-co-Glycolic Acid (PLGA) as Biodegradable Controlled Drug Delivery Carrier", Polymers 3:1377-97 (2011).

Milligan, et al., "Controlling pathological pain by adenovirally driven spinal production of the anit-inflammatory cytokine, interleukin-10", European J. of Neuroscience, 21:2136-48 (2005).

Milligan, et al., "Controlling neuropathic pain by adeno-associated virus driven production of the anti-inflammatory cytokine, interleukin-10", Molecular Pain, published Feb. 25, 2005, pp. 1-13.

Milligan, et al., Intrathecal polymer-based interleukin-10 gene delivery for neuropathic pain, Neuron Glia Biology, 2:1-16 (2007).

Milligan, et al., "Repeated intrathecal injections of plasmid DNA encoding interleukin-10 produce prolonged reversal of neuropathic pain", Pain, 126:294-308 (2006).

Moore, et al., "Interleukin-10 and the Interleukin-10 Receptor", Annu. Rev. Immunol. 19:683-765 (2001).

Pahan, et al., "Interleukin-10 and Interleukin-13 Inhibit Proinflammatory Cytokine-Induced Ceramide Production Through the Activation of Phosphatidylinositol 3-Kinase", J. of Neurochemistry, 75(2):576-82 (2000).

Parsa, et al., "A Comparison Between Polymeric Microsphere and Bacterial Vectors for Macrophage P388D1 Gene Delivery", Pharmaceutical Research, 25(5):1202-08 (2008).

Sawada, et al., "Interleukin-10 Inhibits Both Production of Cytokines and Expression of Cytokine Receptors in Microglia", J. of Neurochemistry, 72(4):1466-71 (1999).

Shakweh, et al., "Poly (lactide-co-glycolide) particleas of different physicochemical properties and their uptake by peye's patches in mice", Eur. J. of Pharmaceutics and Biopharmaceutics, 61:1-13 (2005).

Sloane, et al., "Aniti-inflammatory cytokine gene therapy decreases sensory and motor dysfunction in experimental Multiple Sclerosis: MOG-EAE behavioral and anatomical symptom treatment with cytokine gene therapy", Brain, Behavior and Immunity, 23:92-100 (2009).

Sloane, et al., "Long-term control of neuropathic pain in a non viral gene therapy paradigm", Gene Therapy, 16:470-75 (2009).

Soderquist, et al., "Sustained resolucation of neuropathic pain following microparticle-mediated intrathecal delivery of anti-inflammatory interleukin-10 plasmid DNA", poster, one page (2008).

Soderquist, et al., "Micropartical-Mediated Delivery of Interleukin-10 Plasmid DNA for the treatment of neuropathic pain", poster abstract, one page (2008).

Soderquist, et al. "Release of Plasmid DNA-Encoding IL-10 from PLGA Microparticles Facilitates Long-Term Reversal of Neuropathic Pain Following a Single Intrathecal Administration", Pharmaceutical Research, 27(5):841-54 (2010).

Tinsley-Brown, et al., "Formulation of poly(D,L-lactic-co-glycolic acid) microparticles for rapid plasmid DNA delivery", J. of Controlled Release, 66:229-41 (2000).

Watkins, et al., "The "Toll" of Opioid-Induced Glial Activation: Improving the Clinical Efficacy of Opioids by Targeting Glia", Trends in Pharmaceutical Sciences, p. 1-11 (2009).

St. Clair, "Interleukin 10 treatment for rheumatoid arthritis", Am. Rheum. Dis. 58(Supp I):99-102 (1999).

Vieira-Sousa, et al., "Synovial Tissue Response to Treatment in Rheumatoid Arthritis", The Open Rheumatology Journal, 5(Supp I:M4):115-22 (2011).

Sloane, et al., "Immunological priming potentiates non-viral anti-inflammatory gene therapy treatment of neuropathic pain: Harnessing innate immuniuty to enhance gene therapy", Molecular Therapy, 16(10):1210-22 (2009).

International Search Report for PCT/US2014/047071 dated Nov. 28, 2014, all pages.

International Search Report for PCT/US2013/20542 dated Jan. 7, 2013, all pages.

U.S. Appl. No. 14/066,581, filed Oct. 29, 2013, Watkins et al.

U.S. Appl. No. 16/094,006, filed Oct. 16, 2018, Forsayeth et al.

PCT/US2004/016894, Jan. 13, 2005, International Search Report and Written Opinion.

PCT/US2004/016894, Jan. 3, 2006, International Preliminary Report on Patentability.

PCT/US2014/047071, Jan. 28, 2016, International Preliminary Report on Patentability.

PCT/US2014/047071, Nov. 28, 2014, International Search Report and Written Opinion.

PCT/US2006/020864, Dec. 6, 2007, International Preliminary Report on Patentability.

PCT/US2006/020864, Dec. 20, 2006, International Search Report and Written Opinion.

PCT/US2017/028755, Jul. 26, 2017, International Search Report and Written Opinion.

PCT/US2017/028755, Nov. 1, 2018, International Preliminary Report on Patentability.

PCT/US2006/016594, Nov. 6, 2007, International Preliminary Report on Patentability.

PCT/US2006/016594, May 31, 2007, International Search Report and Written Opinion.

PCT/US2013/020542, Jul. 17, 2014, International Preliminary Report on Patentability.

PCT/US2013/020542, Mar. 14, 2013, International Search Report and Written Opinion.

(56) References Cited

OTHER PUBLICATIONS

PCT/US2006/020863, Feb. 7, 2007, International Search Report and Written Opinion.
PCT/US2006/020863, Dec. 6, 2007, International Preliminary Report on Patentability.
International Search Report and Written Opinion, dated Jan. 13, 2005, in connection with PCT/US2004/016894.
International Preliminary Report on Patentability, dated Jan. 3, 2006, in connection with PCT/US2004/016894.
International Preliminary Report on Patentability, dated Jan. 28, 2016, in connection with PCT/US2014/047071.
International Search Report and Written Opinion, dated Nov. 28, 2014, in connection with PCT/US2014/047071.
International Preliminary Report on Patentability, dated Dec. 6, 2007, in connection with PCT/US2006/020864.
International Search Report and Written Opinion, dated Dec. 20, 2006, in connection with PCT/US2006/020864.
International Search Report and Written Opinion, dated Jul. 26, 2017, in connection with PCT/US2017/028755.
International Preliminary Report on Patentability, dated Nov. 1, 2018, in connection with PCT/US2017/028755.
International Preliminary Report on Patentability, dated Nov. 6, 2007, in connection with PCT/US2006/016594.
International Search Report and Written Opinion, dated May 31, 2007, in connection with PCT/US2006/016594.
International Preliminary Report on Patentability, dated Jul. 17, 2014, in connection with PCT/US2013/020542.
International Search Report and Written Opinion, dated Mar. 14, 2013, in connection with PCT/US2013/020542.
International Search Report and Written Opinion, dated Feb. 7, 2007, in connection with PCT/US2006/020863.
International Preliminary Report on Patentability, dated Dec. 6, 2007, in connection with PCT/US2006/020863.
Adachi et al., Gene transfer of Fc-fusion cytokine by in vivo electroporation: application to gene therapy for viral myocarditis. Gene Ther. May 2002;9(9):577-83. PubMed PMID: 11973633.
Altschul et al., Gapped BLAST and PSI-BLAST: a new generation of protein database search programs. Nucleic Acids Res. Sep. 1, 1997;25(17):3389-402.
Andreansky et al., Treatment of intracranial gliomas in immunocompetent mice using herpes simplex viruses that express murine interleukins. Gene Ther. Jan. 1998;5(1):121-30.
Baron, Mechanisms of disease: neuropathic pain—a clinical perspective. Nat Clin Pract Neurol. Feb. 2006;2(2):95-106.
Bouard et al., Viral vectors: from virology to transgene expression. Br J Pharmacol. May 2009;157(2):153-65. doi: 10.1038/bjp.2008.349.
Bullitt et al., Intracranial tumors in patients with facial pain. J Neurosurg. Jun. 1986;64(6):865-71.
Burger et al., Systemic mannitol-induced hyperosmolality amplifies rAAV2-mediated striatal transduction to a greater extent than local co-infusion. Mol Ther. Feb. 2005;11(2):327-31.
Cavazzana-Calvo et al., Gene therapy for severe combined immunodeficiency: are we there yet? J Clin Invest. Jun. 2007;117(6):1456-65.
Chan, Optic neuritis in multiple sclerosis. Ocul Immunol Inflamm. Sep. 2002;10(3):161-86.
Chattopadhyay et al., Effect of single amino acid mutations in the conserved GDNQ motif of L protein of Rinderpest virus on RNA synthesis in vitro and in vivo. Virus Res. Feb. 2004;99(2):139-45.
Chen et al., Surface properties, more than size, limiting convective distribution of virus-sized particles and viruses in the central nervous system. J Neurosurg. Aug. 2005;103(2):311-9.
Choate et al., Direct cutaneous gene delivery in a human genetic skin disease. Hum Gene Ther. Sep. 20, 1997;8(14):1659-65.
Crepaldi et al., Up-regulation of IL-10R1 expression is required to render human neutrophils fully responsive to IL-10. J Immunol. Aug. 15, 2001;167(4):2312-22.
Cua et al., Central nervous system expression of IL-10 inhibits autoimmune encephalomyelitis. J Immunol. Jan. 1, 2001;166(1):602-8.
Dai et al., Cloning, sequencing of human interleukin-10 cDNA and construction of RT its eukarvotic expression vector. Journal of Harbin Medical University. 35:4-6(2001).
Dengler et al., Improvement of spinal non-viral IL-10 gene delivery by D-mannose as a transgene adjuvant to control chronic neuropathic pain, J. Neuroinflammation 11 (92):1-21 (2014).
Eck et al, Goodman & Gilman's the Pharmacological Basis of Therapeutics, McGraw-Hill, New York, 1996;77-101.
Genbank Accession No. P22301 (Aug. 1, 1991).
Gesser et al., Identification of functional domains on human interleukin 10. Proc Natl Acad Sci U S A. Dec. 23, 1997;94(26):14620-5.
Goodman et al., Synthesis and characterization of rat interleukin-10 (IL-10) cDNA clones from the RNA of cultured OX8-OX22-thoracic duct T cells. Biochem Biophys Res Commun. Nov. 30, 1992;189(1):1-7.
Gorecki, Prospects and problems of gene therapy: an update. Expert Opin Emerg Drugs. Oct. 2001;6(2):187-98.
Goudy et al., Adeno-associated virus vector-mediated IL-10 gene delivery prevents type 1 diabetes in NOD mice. Proc Natl Acad Sci U S A. Nov. 20, 2001;98(24):13913-8.
Hao et al., Herpes simplex virus (HSV) vector expressing soluble TNF a.-receptor and IL-4 produces persistent antinociception in neuropathic pain Washington D. C., Society for Neuroscience, Program No. 131.8 (2003).
Jiang et al., Sustained expression of Fc-fusion cytokine following in vivo electroporation and mouse strain differences in expression levels. J Biochem. Apr. 2003;133(4):423-7.
Johnson-Saliba et al., Gene therapy: optimising DNA delivery to the nucleus. Curr Drug Targets. Dec. 2001;2(4):371-99.
Josephson et al., Crystal structure of the IL-10/IL-10R1 complex reveals a shared receptor binding site. Immunity. Jul. 2001;15(1):35-46.
Khoury et al., A comparative study on intra-articular versus systemic gene electrotransfer in experimental arthritis. J Gene Med. Aug. 2006;8(8):1027-36.
Kodama et al., The features and shortcomings for gene delivery of current non-viral carriers. Curr Med Chem. 2006;13(18):2155-61.
Kuroda et al., A comparative analysis of constitutive and cell-specific promoters in the adult mouse hippocampus using lentivirus vector-mediated gene transfer. J Gene Med. Nov. 2008;10(11):1163-75. doi: 10.1002/jgm.1249.
Laughlin et al., Cytokine involvement in dynorphin-induced allodynia. Pain. Feb. 2000;84(2-3):159-67.
Lechman et al., Direct adenoviral gene transfer of viral IL-10 to rabbit knees with experimental arthritis ameliorates disease in both injected and contralateral control knees. J Immunol. Aug. 15, 1999;163(4):2202-8.
Lentz et al., Viral vectors for gene delivery o the central nervous system. Neurobiol Dis. Nov. 2012;48(2):179-88. doi:10.1016/j.nbd.2011.09.014. [Author Manuscript].
Lin et al., Relation of an interleukin-10 promoter polymorphism to graft-versus-host disease and survival after hematopoietic-cell transplantation. N Engl J Med. Dec. 4, 2003;349(23):2201-10.
Martin et al., Neuropathic pain in cancer patients: mechanisms, syndromes, and clinical controversies. J Pain Symptom Manage. Aug. 1997;14(2):99-117.
Mata et al., Applications of gene therapy to the treatment of chronic pain. Curr Gene Ther. Feb. 2008;8(1):42-8. [Author Manuscript].
Meuli-Simmen et al., Gene expression along the cerebral-spinal axis after regional gene delivery. Hum Gene Ther. Nov. 1, 1999;10(16):2689-700.
Miller, Drug targeting. Breaking down barriers. Science. Aug. 16, 2002;297(5584):1116-8.
Milligan et al., 10th Congress on Pain: Abstract 392-P26, 135. Aug. 19, 2002.
Milligan et al., 530. Spinal Interleukin-10 (IL-10) Gene Therapy Using Viral and Non-Viral Vectors Controls Inflammatory- and Chronic Constriction Injury-Induced Pain States in Rat. Molecular Therapy. May 2004;9(1):S200-S201.

(56) References Cited

OTHER PUBLICATIONS

Milligan et al., Controlling Neuropathic Pain by Adeno-Associated Virus Driven Production of the Anti-Inflammatory Cytokine, Interleukin-10, Molecular Paid, I:9 (2005), doi:10.1186/1744-8069-I-9.
Milligan et al., Controlling Pathological Pain by Adenovirally Driven Spinal Production of the Anti-Inflammatory Cytokine, Interleukin-10, European J Neuroscience. 2005;21:2136-2148.
Milligan et al., Intrathecal polymer-based interleukin-10 gene delivery for neuropathic pain, Neuron Glia Biology. 2007;2:1-16.
Milligan et al., Society for Neuroscience, 2002, Presentation No. 656.19, Neuroscience 2002 Abstract.
Mu et al., IL-10 suppresses chemokines, inflammation, and fibrosis in a model of chronic renal disease. J Am Soc Nephrol. Dec. 2005;16(12):3651-60.
Nishikawa et al., Nonviral vectors in the new millennium: delivery barriers in gene transfer. Hum Gene Ther. May 20, 2001;12(8):861-70.
Okamoto et al., Pro- and anti-inflammatory cytokine gene expression in rat sciatic nerve chronic constriction injury model of neuropathic pain. Exp Neurol. Jun. 2001;169(2):386-91.
Pettit et al., The development of site-specific drug-delivery systems for protein and peptide biopharmaceuticals. Trends Biotechnol. Aug. 1998;16(8):343-9.
Pfiefer et al., Gene therapy: promises and problems. Annu Rev Genomics Hum Genet. 2001;2:177-211.
Plunkett et al., Effects of interleukin-10 (IL-10) on pain behavior and gene expression following excitotoxic spinal cord injury in the rat. Exp Neurol. Mar. 2001;168(1):144-54.
Raghavendra et al., The role of spinal neuroimmune activation in morphine tolerance/hyperalgesia in neuropathic and sham-operated rats. J Neurosci. Nov. 15, 2002;22(22):9980-9.
Shoji et al. Current status of delivery systems to improve target efficacy of oligonucleotides. Curr Pharm Des. 2004;10(7):785-96.
Skolnick et al., From genes to protein structure and function: novel applications of computational approaches in the genomic era. Trends Biotechnol. Jan. 2000;18(1):34-9.
Smallwood et al., Different substitutions at conserved amino acids in domains II and III in the Sendai L RNA polymerase protein inactivate viral RNA synthesis. Virology. Dec. 5, 2002;304(1):135-45.
Storek et al., Intrathecal long-term gene expression by self-complementary adeno-associated virus type 1 suitable for chronic pain studies in rats. Mol Pain. Jan. 30, 2006;2:4.
Tomasinsig et al., The cathelicidins—structure, function and evolution. Curr Protein Pept Sci. Feb. 2005;6(1):23-34.
Vakaet et al., Pain control by ionizing radiation of bone metastasis. Int. J. Dev. Biol. 2004;48:599-606.
Verma et al., Gene therapy—promises, problems and prospects. Nature. Sep. 18, 1997;389(6648):239-42.
Vieira et al., Isolation and expression of human cytokine synthesis inhibitory factor cDNA clones: homology to Epstein-Barr virus open reading frame BCRFI. Proc Natl Acad Sci U S A. Feb. 15, 1991;88(4):1172-6.
Wagner et al., Anti-inflammatory interleukin-10 therapy in CCI neuropathy decreases thermal hyperalgesia, macrophage recruitment, and endoneurial TNF-alpha expression. Pain. Jan. 1998;74(1):35-42.
Watkins et al., Glia: a novel drug discovery target for clinical pain. Nat Rev Drug Discov. Dec. 2003;2(12):973-85.
Watkins et al., Immune regulation of central nervous system functions: from sickness responses to pathological pain. J Intern Med. Feb. 2005;257(2):139-55.
Whalen et al., Adenoviral transfer of the viral IL-10 gene periarticularly to mouse paws suppresses development of collagen-induced arthritis in both injected and uninjected paws. J Immunol. Mar. 15, 1999;162(6):3625-32.
Yang et al., Sustained expression of naked plasmid DNA encoding hepatocyte growth factor in mice promotes liver and overall body growth. Hepatology. Apr. 2001;33(4):848-59.
Yao et al., Interleukin-2 gene has superior antinociceptive effects when delivered intrathecally. Neuroreport. May 7, 2002;13(6):791-4.
Yoon et al., Same structure, different function crystal structure of the Epstein-Barr virus IL-10 bound to the soluble IL-10R1 chain. Structure. Apr. 2005;13(4):551-64.
Zdanov et al., Crystal structure of human interleukin-10 at 1.6 A resolution and a model of a complex with its soluble receptor. Protein Sci. Oct. 1996;5(10):1955-62.
Zdanov et al., Crystal structure of interleukin-10 reveals the functional dimer with an unexpected topological similarity to interferon gamma. Structure. Jun. 15, 1995;3(6):591-601.
Zhang et al., Signal peptide prediction based on analysis of experimentally verified cleavage sites. Protein Sci. Oct. 2004;13(10):2819-24.
Zhang et al., Suppression of early experimental osteoarthritis by gene transfer of interleukin-1 receptor antagonist and interleukin-10. J Orthop Res. Jul. 2004;22(4):742-50.
Zheng et al., Administration of noncytolytic IL-10/Fc in murine models of lipopolysaccharide-induced septic shock and allogeneic islet transplantation. J Immunol. May 15, 1995;154(10):5590-600.

* cited by examiner

METHODS FOR THE TREATMENT OF INFLAMMATORY JOINT DISEASE

CROSS-REFERENCE TO RELATED APPLICATIONS

This application is a national stage filing under 35 U.S.C. § 371 of international PCT application, PCT/US2014/047071, filed Jul. 17, 2014, which claims the benefit of U.S. Provisional Patent Application No. 61/847,851, filed Jul. 18, 2013, each of which is incorporated herein by reference.

STATEMENT REGARDING FEDERALLY FUNDED RESEARCH

This invention was made with government support under grant number U44-N5071642 awarded by the National Institute of Health. The government has certain rights in the invention.

FIELD OF THE INVENTION

This invention relates to treating clinical conditions associated with inflammatory diseases of the joints and symptoms associated therewith by administering to the inflamed joint a therapeutic anti-inflammatory composition comprising a bacterial or viral interleukin-10 (IL-10) expression construct.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under applicable statutory provisions.

Joint pain can flare up for any number of reasons, as a result of, e.g., over a hundred different arthritic conditions—of which rheumatoid arthritis and osteoarthritis are the most common—as well as tendonitis, bursitis, inflammation of the ligament, synovitis, gout, and systemic lupus erythematosus. When injured, a chain of events in the immune system known as the inflammatory cascade is triggered, causing redness, swelling and pain. Next, anti-inflammatory compounds take over to heal the area once the threat is diminished. When this process—known as local or acute inflammation takes place—it is a sign of a healthy immune system. However, if inflammation persists it can lead to a more chronic condition.

Current treatments for inflammatory diseases of the joint such as rheumatoid and osteo-arthritis, tendonitis, synovitis and the like remain suboptimal. Identifying treatments that would require less frequent administration would impact significantly the quality of life for patients with inflammatory joint disease; however, despite substantial research into and development of therapies for such conditions there is still a large unmet need for safe, effective, and easy-to-administer treatments.

SUMMARY OF THE INVENTION

The present invention provides methods for treating inflammatory diseases of the joints, symptoms associated with inflammatory diseases of the joints, and slowing disease progression by administering to a subject, typically injected into the joint, a vector expressing an interleukin-10 (IL-10) coding sequence. In some embodiments, the IL-10 expression construct is encapsulated in biodegradable microparticles, and in certain aspects of these embodiments, the microparticles are suspended in a diluent to form a therapeutic composition.

In yet other, alternative embodiments, the therapeutic compositions of the present invention are IL-10 expression constructs—with either a bacterial or viral backbone—that are delivered as "naked" DNA. That is, the IL-10 expression constructs are delivered without encapsulation. In such embodiments, the IL-10 expression constructs are delivered in conjunction with one or more diluents, and in preferred aspects of these embodiments, the IL-10 expression construct is delivered in conjunction with one or more adjuvants. In some aspects of this embodiment, the one or more adjuvants may be administered to a subject at the time of the administration of the IL-10 expression construct or up to 10 days before administration of the IL-10 expression construct, e.g., as a "pretreatment".

In some aspects, the joint inflammation is in the knee, elbow, wrist, ankle, hip, shoulder, or spine. Conditions treatable by the methods of the present invention include rheumatoid arthritis and osteoarthritis, as well as tendonitis, bursitis, inflammation of the ligament, synovitis, gout, and systemic lupus erythematosus.

Thus, some embodiments of the invention provide methods for treatment of inflammatory diseases of the joints or disorders or symptoms associated therewith in a subject comprising administering to the subject a therapeutic anti-inflammatory IL-10 compound comprising: plasmid DNA comprising a bacterial backbone and at least one IL-10 coding sequence and a diluent; where the therapeutic anti-inflammatory IL-10 compound provides a therapeutically effective dose to a joint at about 1 µg DNA to about 1000 µg DNA, or about 5 µg DNA to about 900 µg DNA, or about 10 µg DNA to about 850 µg DNA, or about 20 µg DNA to about 800 µg DNA, or about 25 µg DNA to about 750 µg DNA, or about 40 µg DNA to about 500 µg DNA, or about 50 µg DNA to about 250 µg DNA, or about 5 µg DNA to about 200 µg DNA, though preferably about 2.5 µg DNA to about 500 µg DNA. In other embodiments, a viral vector is used as an alternative to a bacterial vector.

In some preferred embodiments of the present invention, the IL-10 therapeutic compounds of the present invention (i.e., encapsulated or naked DNA) are administered with one or more adjuvants. The adjuvants of the invention are biocompatible agents that may be administered simultaneously with the IL-10 therapeutic compounds or as a pre-treatment before the IL-10 therapeutic compounds are administered. Adjuvants that are particularly preferred include but are not limited to mannose, sucrose, glucose, calcium phosphate, dendrimers, liposomes including cationic liposomes, and oligodeoxynucleotides. The adjuvants of the present invention in preferred embodiments are those adjuvants that increase uptake or efficacy of the IL-10 expression construct. Concurrent administration or pretreatment includes administering to the joint about 5 µg adjuvant to about 1000 µg adjuvant, or about 10 µg adjuvant to about 750 µg adjuvant, or about 50 µg adjuvant to about 500 µg adjuvant, or about 25 µg adjuvant to about 750 µg adjuvant at the time of or up to 10 days prior to the administration of the therapeutic anti-inflammatory IL-10 compound.

Other alternative embodiments provide methods for treatment of inflammatory diseases of the joints comprising administering to the subject a therapeutic anti-inflammatory composition comprising: an IL-10 expression construct;

microparticles encapsulating the IL-10 expression construct; and a diluent; where the therapeutic microparticle composition provides a therapeutically effective dose to a joint at about 20 µg DNA to about 1000 µg DNA, or about 25 µg DNA to about 750 µg DNA, or about 50 µg DNA to about 500 µg DNA, or about 50 µg DNA to about 250 µg DNA, or about 50 µg DNA to about 200 µg DNA, or or about 25 µg DNA to about 100 µg DNA.

Yet other embodiments of the present invention provide methods for slowing progression of inflammatory diseases of the joints in a subject comprising administering to the subject a therapeutic anti-inflammatory IL-10 compound comprising: plasmid DNA comprising a bacterial backbone and at least one IL-10 coding sequence, where the therapeutic IL-10 expression construct provides a therapeutically effective dose to a joint at about 1 µg DNA to about 1000 µg DNA, about 5 µg DNA to about 900 µg DNA, about 10 µg DNA to about 850 µg DNA, about 20 µg DNA to about 800 µg DNA, or about 25 µg DNA to about 750 µg DNA, or about 50 µg DNA to about 500 µg DNA, or about 50 µg DNA to about 250 µg DNA, or about 50 µg DNA to about 200 µg DNA, or about 25 µg DNA to about 100 µg DNA. In such embodiments, an adjuvant preferably is administered with the therapeutic anti-inflammatory IL-10 compound or up to 10 days before administration of the therapeutic anti-inflammatory IL-10 compound, e.g., as a pretreatment.

Optionally in the embodiments described, the IL-10 expression construct comprises at least one nuclear targeting sequence located either from 100 to 2000 bp 5' to the at least one IL-10 coding sequence and/or from 150 to 450 bp 3' to the at least one IL-10 coding sequence. In other aspects of the present invention, the IL-10 expression construct comprises two nuclear targeting sequences where one nuclear targeting sequence is positioned from 100 to 2000 bp 5' of the at least one IL-10 coding sequence, and one nuclear targeting sequence is positioned from 150 to 450 bp 3' of the at least one coding sequence.

Preferably, the therapeutic composition is administered by injection into the joint(s), and in preferred embodiments the therapeutic composition is administered by intra-articular injection.

In some aspects, the nucleic acid sequence encoding interleukin-10 has an amino acid substitution for wildtype phenylalanine at amino acid position 129, and in some aspects, the amino acid substitution is selected from the group of serine, alanine, threonine or cysteine. In some aspects, the nucleic acid sequence encoding interleukin-10 encodes IL-10$^{F129S}$. In yet other aspects, the IL-10 expression construct comprises at least one nuclear targeting sequence 5' to the IL-10 coding sequence, and in some aspects, IL-10 expression construct comprises at least one nuclear targeting sequence 3' to the IL-10 coding sequence.

In some aspects of the present invention, the microparticles comprise one or more of poly(2-hydroxy ethyl methacrylate), poly(N-vinyl pyrrolidone), poly(methyl methacrylate), poly(vinyl alcohol), poly(acrylic acid), polyacrylamide, poly(ethylene-co-vinyl acetate), poly(ethylene glycol), poly(methacrylic acid), polylactides (PLA), polyglycolides (PGA), poly(lactide-co-glycolides) (PLGA), polyanhydrides, polycaprolactone, poly-3-hydroxybutyrate or polyorthoesters. In certain aspects of the present invention, the microparticles comprise PLGA. In other aspects of the invention, the microparticles comprise a mixture of biodegradable polymers representing different, complimentary release profiles.

In certain embodiments of the methods, the therapeutic anti-inflammatory IL-10 expression construct (and any adjuvant or "pretreatment" adjuvant), is delivered approximately every 40 to 120 days as needed for therapeutic effect, e.g., up to one year. In other embodiments, the therapeutic anti-inflammatory composition is delivered approximately every 40 to 120 days as needed for therapeutic effect for greater than one year. In yet other embodiments, the therapeutic anti-inflammatory composition is delivered as needed for therapeutic effect approximately every 40 to 120 days, as needed, for the life of the subject.

The methods of the present invention also may be employed as a research tool to identify pharmaceuticals, small molecules and/or biologics that may be used in conjunction in a "cocktail" with the therapeutic IL-10 expression construct compositions.

DETAILED DESCRIPTION OF THE INVENTION

Definitions

Figure 1:
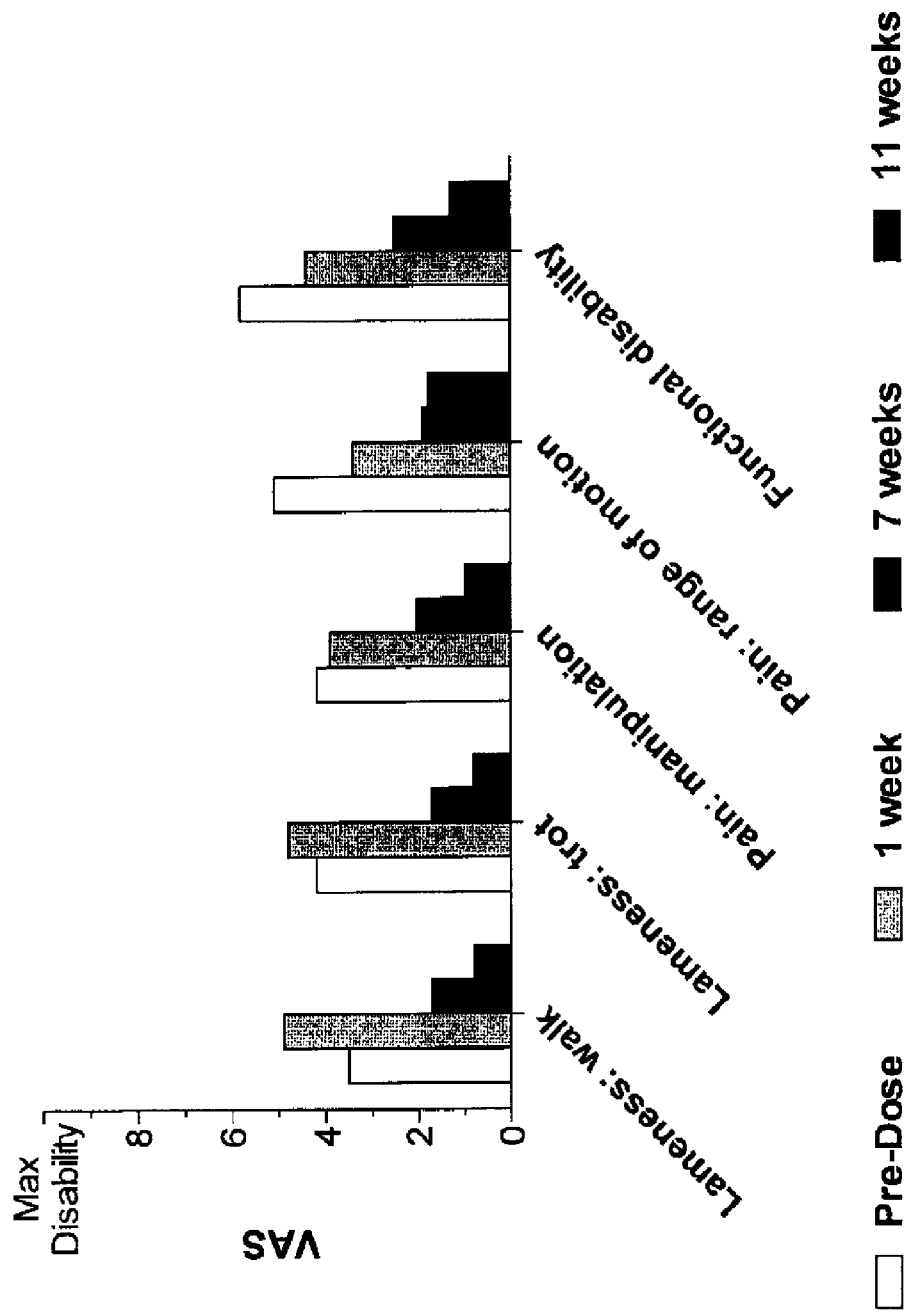
FIG. 1 shows results in the form of bar graphs illustrating clinical assessment of the functional improvement and pain reduction achieved treating osteoarthritis of forelimb joints in canines after administration of the therapeutic IL-10 expression constructs of the present invention.

Unless defined otherwise, all technical and scientific terms used herein have the same meaning as commonly understood by one of ordinary skill in the art to which this invention belongs. All publications, published patent applications and patents mentioned herein are incorporated by reference in their entirety for the purpose of describing and disclosing devices, animal models, formulations and methodologies that may be used in connection with the presently described invention.

The term adjuvant as used herein refers to a pharmacological or immunological agent that modifies the effect of other agents. In the context of the present invention, an adjuvant is used to increase the efficacy of the therapeutic IL-10 anti-inflammatory compound. Adjuvants of particular utility in the present invention include those that enhance the uptake or efficacy of the IL-10 expression construct by, e.g., macrophages or other immune cells present in the synovial fluid of the joint.

The term "anti-inflammatory" as used herein refers to decreasing the action or production of one or more proinflammatory cytokines or proteins produced by nerves, neurons, glial cells, endothelial cells, fibroblasts, muscle, immune cells or other cell types.

The term "anti-inflammatory cytokine" as used herein refers to a protein that decreases the action or production of one or more proinflammatory cytokines or proteins produced by nerves, neurons, glial cells, endothelial cells, fibroblasts, muscle, immune cells or other cell types. Inflammatory cytokines and proteins include, without limitation, interleukin-1 beta (IL-1β), tumor necrosis factor-alpha (TNF-α), interleukin-6 (IL-6), inducible nitric oxide synthetase (iNOS) and the like. Non-limiting examples of anti-inflammatory cytokines include interleukin-10 (IL-10) including viral IL-10, interleukin-4 (IL-4), interleukin-13 (IL-13), alpha-MSII, transforming growth factor-beta 1 (TGFβ1), and the like. Thus, the full-length molecules and fragments of anti-inflammatory cytokines, as well as anti-inflammatory cytokines with modifications, such as deletions, additions and substitutions (either conservative or non-conservative in nature), to the native sequence, are intended for use herein, so long as the anti-inflammatory cytokine is therapeutically effective. Modifications may be deliberate, as through site-directed mutagenesis, or may be accidental, such as through mutations of hosts which produce the proteins or errors due to PCR amplification. Accordingly, active proteins are typically substantially homologous to the parent sequence, e.g., proteins are typically about 70 . . . 80 . . . 85 . . . 90 . . . 95 . . . 98 . . . 99%, etc. homologous to the parent sequence.

A "coding sequence" of an anti-inflammatory cytokine or a sequence that "encodes" an anti-inflammatory cytokine is a nucleic acid molecule that is transcribed (in the case of DNA) and translated (in the case of mRNA) into a polypeptide in vivo when placed under the control of appropriate control sequences. The boundaries of the coding sequence are determined by nucleotides corresponding to a start codon at the amino terminus and nucleotides corresponding to a translation stop codon at the carboxy terminus.

The term DNA "control sequences" refers collectively to promoter sequences, polyadenylation signals, transcription termination sequences, upstream regulatory domains, origins of replication, internal ribosome entry sites, enhancers, and the like, which collectively provide for the replication, transcription and translation of a coding sequence in a recipient cell. Not all of these types of control sequences need to be present so long as the selected coding sequence is capable of being replicated, transcribed and translated in an appropriate host cell.

The terms "effective amount" or "therapeutically effective amount" of a therapeutic IL-10 expression construct used in the methods of the invention refer to a nontoxic but sufficient amount of the IL-10 expression construct to provide the desired response, such as a decrease in inflammation of the joints, relief from symptoms caused by inflammatory diseases of the joints and/or preventing progression of joint damage due to inflammatory diseases of the joints. The exact amount required will vary from subject to subject, depending on the species, age, and general condition of the subject, the severity of the condition being treated, and the particular IL-10 expression construct to be delivered whether the IL-10 expression construct is delivered in a microparticle or as naked DNA, mode of administration (e.g., intra-articular injection), and the like. Dosage parameters for the present methods are provided herein; however, optimization of an appropriate "effective" amount in any individual case may be determined by one of ordinary skill in the art using the methods set forth herein and routine experimentation.

The term "excipient" or "diluent" refers to an inert substance added to a therapeutic composition of the invention to facilitate administration of the therapeutic IL-10 expression construct. Examples, without limitation, of excipients include saline, calcium carbonate, calcium phosphate, various sugars and types of starch, cellulose derivatives, gelatin, hyaluronic acid optionally formulated with a surfactant, Plurnoic F-68, vegetable oils and polyethylene glycols.

By "isolated" when referring to a nucleotide sequence, is meant that the expression construct is present in the substantial absence of other biological macromolecules of the same type. Thus, an "isolated nucleic acid molecule which encodes a particular polypeptide" refers to a nucleic acid molecule which is substantially free of other nucleic acid molecules that do not encode the subject polypeptide; however, the molecule may include some additional bases or moieties that do not deleteriously affect the basic characteristics of the composition.

The term "joint" refers to an anatomical structure where two bones meet, including the ligaments that connect the bones to one another, the tendons that attach muscles to the bones, the joint capsule, bursae and synovium. Joints that can be treated with the methods herein include fixed, hinge, pivot or ball-and-socket joints.

The term "joint inflammation" refers to all types of arthritis caused by inflammation where rheumatoid arthritis, osteoarthritis are the most common, as well as tendonitis, bursitis, inflammation of the ligament, synovitis, gout, and systemic lupus erythematosus.

The term "nuclear targeting sequence" refers to a nucleic acid sequence which functions to improve the expression efficiency of an anti-inflammatory cytokine in a cell.

"Operably linked" refers to an arrangement of elements where the components so described are configured so as to perform their usual function. Thus, control sequences operably linked to a coding sequence are capable of effecting the expression of the coding sequence. The control sequences need not be contiguous with the coding sequence so long as they function to direct the expression thereof. Thus, for example, intervening untranslated yet transcribed sequences can be present between a promoter sequence and the coding sequence and the promoter sequence can still be considered "operably linked" to the coding sequence.

The term "promoter" is used herein in its ordinary sense to refer to a nucleotide region comprising a DNA regulatory sequence, wherein the regulatory sequence is derived from a gene that is capable of binding RNA polymerase and initiating transcription of a downstream (3'-direction) coding sequence. Transcription promoters can include "inducible promoters" (where expression of a polynucleotide sequence operably linked to the promoter is induced by an analyte, cofactor, regulatory protein, etc.), "repressible promoters" (where expression of a polynucleotide sequence operably linked to the promoter is induced by an analyte, cofactor, regulatory protein, etc.), and "constitutive promoters".

For the purpose of describing the relative position of nucleotide sequences in a particular nucleic acid molecule throughout the instant application, such as when a particular nucleotide sequence is described as being situated "upstream," "downstream," "3 prime (3')" or "5 prime (5')" relative to another sequence, it is to be understood that it is the position of the sequences in the "sense" or "coding" strand of a DNA molecule that is being referred to as is conventional in the art.

The term "research tool" as used herein refers to any methods of the invention using the therapeutic IL-10 expression constructs for scientific inquiry, either academic or commercial in nature, including the development of other pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The terms "subject", "individual" or "patient" may be used interchangeably herein and refer to a vertebrate, preferably a mammal.

The term "therapeutic composition" or "therapeutic anti-inflammatory composition" as used herein refers to a composition that has the ability to decrease inflammation of the joints, provide relief from symptoms caused by inflammatory diseases of the joints and/or prevent progression of joint damage due to inflammatory diseases of the joints as measured in any of the known animal models or by assessment performed in humans.

"Treatment" or "treating" joint inflammation includes: (1) decreasing inflammation of the joint or causing the inflammation to occur with less intensity in a subject that may be predisposed to joint inflammation but does not yet experience or display symptoms, or (2) inhibiting joint inflammation, i.e., arresting the development of or reversing symptoms or physiological damage caused by inflammation.

A "viral vector" as used herein is a recombinantly produced virus or viral particle that comprises an IL-10 expression construct to be delivered into a host cell, either in vivo, ex vivo or in vitro. Examples of viral vectors include retroviral vectors, lentiviral vectors, adenovirus vectors, adeno-associated virus vectors, alphavirus vectors and the like.

The practice of the techniques described herein may employ, unless otherwise indicated, conventional techniques and descriptions of organic chemistry, polymer technology, molecular biology (including recombinant techniques), cell biology, biochemistry, and sequencing technology, which are within the skill of those who practice in the art. Specific illustrations of suitable techniques can be had by reference to the examples herein. However, other equivalent conventional procedures can, of course, also be used. Such conventional techniques and descriptions can be found in standard laboratory manuals such as LeDoux (Ed.) (2005), *Animal Models of Movement Disorders* (Academic Press); Chow, et al., (2008), *Using Animal Models in Biomedical Research* (World Scientific Publishing Co.); Weir and Blackwell (Eds.), *Handbook of Experimental Immunology*, Vols. I-IV (Blackwell Scientific Publications); Creighton (1993), *Proteins: Structures and Molecular Properties* (W.H. Freeman and Company); Sambrook and Russell (2006), *Condensed Protocols from Molecular Cloning: A Laboratory Manual*; and Sambrook and Russell (2002), *Molecular Cloning: A Laboratory Manual* (both from Cold Spring Harbor Laboratory Press); Stryer, L. (1995) *Biochemistry*, Fourth Ed. (W.H. Freeman); Gait (1984), "*Oligonucleotide Synthesis: A Practical Approach*" (IRL Press); Nelson and Cox (2000), Lehninger, *Principles of Biochemistry*, Third Ed. (W. H. Freeman); and Berg et al. (2002) *Biochemistry*, Fifth Ed. (W.H. Freeman); all of which are herein incorporated in their entirety by reference for all purposes.

Note that as used herein and in the appended claims, the singular forms "a," "an," and "the" include plural referents unless the context clearly dictates otherwise.

Where a range of values is provided, it is understood that each intervening value, between the upper and lower limit of that range and any other stated or intervening value in that stated range is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Methods of the Invention

The present invention provides methods for treating inflammatory diseases of the joints, symptoms associated with inflammatory diseases of the joints, and slowing disease progression by administering to a subject—typically injected via intra-articular injection—a vector expressing a therapeutic interleukin-10 (IL-10) expression construct. In some embodiments, the IL-10 expression construct is encapsulated in biodegradable microparticles, and in most aspects of this embodiment, the microparticles are suspended in a diluent to form a therapeutic composition. As an alternative, in preferred embodiments the therapeutic IL-10 expression vector is delivered as a "naked" vector, where the delivery of the naked IL-10 expression vector is accompanied by or preceded by administration of a nucleic acid uptake adjuvant. The nucleic acid uptake adjuvant may be administered either concurrently or up to ten or more days prior to the administration of the naked IL-10 expression vector. The methods of the present invention may be used to treat joint inflammation in the knee, elbow, wrist, ankle, hip, shoulder, or spine. Conditions treatable by the methods of the present invention include rheumatoid arthritis and osteoarthritis, as well as tendonitis, bursitis, inflammation of the ligament, synovitis, gout, and systemic lupus erythematosus.

Thus, the invention generally provides methods for treating inflammatory diseases of the joints and symptoms and physiological damage associated with inflammatory diseases of the joints. The invention also provides for using the methods of the invention in research of inflammatory diseases of the joints, including identifying pharmaceuticals, small molecules and/or biologics that may be used in conjunction (in a "cocktail") with the therapeutic IL-10 expression construct. The methods comprise the step of administering to a subject, preferably by injection into a joint, an IL-10 expression construct comprising a bacterial or viral backbone and at least one IL-10 coding sequence. In some embodiments, the IL-10 expression construct is optionally encapsulated in biodegradable microparticles. The anti-inflammatory compositions are generally suspended in a diluent for delivery to a joint. The IL-10 expression construct may comprise at least one nuclear targeting sequence where the at least one nuclear targeting sequence is 5', 3' or both to the IL-10 coding sequence.

The anti-inflammatory compounds of the present invention may consist of a "naked" bacterial vector or viral vector capable of expressing the at least one IL-10 coding sequence, or the anti-inflammatory compound may consist of a bacterial or viral vector encased in microparticles or other delivery device. Administration of the therapeutic IL-10 expression construct may be accompanied by or preceded by administration of an adjuvant, and in the case of delivery of naked IL-10 expression constructs, a nucleic acid uptake adjuvant may be administered concurrently or up to ten days or more before administration of the naked IL-10 expression construct.

The IL-10 expression construct used in some embodiments of the methods of the present invention comprises a bacterial backbone (plasmid DNA or pDNA) or a viral backbone, at least one IL-10 coding sequence, at least one nuclear targeting sequence 5' (upstream), 3' (downstream) or both of the at least one IL-10 coding sequence, and one or more DNA control sequences. Optionally, the pDNA also may comprise one or more additional anti-inflammatory cytokine coding sequences, and/or a marker sequence to allow for selection of transformed cells during amplification of the pDNA. The bacterial backbone can be any bacterial backbone known to those with skill in the art. Backbones typically selected are those that, e.g., contain or lack appropriate restriction sites to allow ease of cloning, may be produced and isolated with ease, are not immunogenic, and the like. For example, bacterial backbones derived from *E. coli* are of use in the present invention.

The plasmid DNA comprises at least one IL-10 coding sequence. IL-10 coding sequence may code for wildtype IL-10, or the IL-10 may be a mutant IL-10. One mutant IL-10 of interest contains one or more mutations that cause amino acid substitutions, additions or deletions as compared to wildtype IL-10 in the "hinge" region of the IL-10 protein. The human IL-10 protein is a homodimer, where each monomer comprises six alpha helices A→F, the length of which are 21, 8, 19, 20, 12 and 23 amino acids, respectively. Helices A→D of one monomer noncovalently interact with helices E and F of a second monomer, forming a noncovalent V-shaped homodimer. The "hinge" region targeted for mutation according to the present invention comprises the amino acids between the D and E alpha helices on one or both monomers at approximately amino acid position X to position Y of wildtype IL-10. For example, mutant rat and human IL-10 proteins have been described in which the phenylalanine at position 129 of the wildtype sequence has been replaced with a serine residue. (See, e.g., Sommer, et al., WO2006/130580 and Milligan, et al., Pain, 126:294-308 (2006).) The resulting mutant IL-10 is referred to as IL-10$^{F129S}$. Other substitutions for the wildtype phenylalanine at amino acid position 129 may be, e.g., threonine, alanine, or cysteine. Thus the present invention in yet another aspect encompasses one or more substitutions at amino acid position 129 or at other amino acids within the hinge region of the IL-10 protein, or functional equivalents thereof.

Additional anti-inflammatory cytokines of use in the present invention include but are not limited to interleukin-4 (IL-4), interleukin-13 (IL-13), alpha-MSH, transforming growth factor-beta 1 (TGFβ1), and the like.

Nuclear targeting sequences of the present invention are sequences that promote expression of the protein(s) encoded by the at least one IL-10 coding sequence and the optional, additional anti-inflammatory cytokine coding sequence(s). For example, in one aspect the nuclear targeting sequences may bind to nuclear transport chaperone proteins, facilitating uptake of the plasmid DNA by the cell nucleus. Such sequences include but are not limited to interspersed (or dispersed) DNA repeats or repetitive sequences such as transposable elements, flanking or terminal repeats such as the long terminal repeats (LTRs) on retrovirus genomes such as SV40s, tandem repeats, and the inverted terminal repeats (ITRs) of viral genomes such as Adeno-Associated Virus and Adenovirus. In other aspects, the nuclear targeting sequences are sequences that act to bind transcription factors for import into the nucleus, such as enhancer sequences.

In addition to a bacterial backbone, at least one IL-10 coding sequence and optional one or more additional anti-inflammatory cytokine coding sequences and, optionally, one or more nuclear targeting sequences, the plasmid DNA of the present invention comprises one or more DNA control sequences, such as promoter sequences, polyadenylation signals, transcription termination sequences, upstream regulatory domains, origins of replication, internal ribosome entry sites and the like, which collectively provide for the replication, transcription and translation of the anti-inflammatory cytokine coding sequence(s) in a recipient cell. Not all of these control sequences need always be present so long as the anti-inflammatory cytokine coding sequences are capable of being replicated, transcribed and translated in an appropriate host cell. Promoter sequences of use in the present invention include but are not limited to chicken or human β-actin promoters, cytomegalovirus immediate early promoters, glyceraldehydes 3-phosphate dehydrogenase (GADPH) promoters, elongation factor 1α (eF1α) promoter, GFAP promoter, murine leukemia virus (MLV) promoter, herpes simples virus thymidine kinase (TK) promoter, and woodchuck hepatitis virus post-transcriptional regulatory element (WPRE) promoters; upstream regulatory domains of use in the present invention include but are not limited to cytomegalovirus immediate early promoter enhancers, mouse mammary tumor virus (MMTV) enhancer and simian virus 40 (SV40) enhancer; and polyadenylation signals of interest in the present invention include but are not limited to SV40 polyadenylation signal, bovine growth hormone polyadenylation signal, and synthetic polyadenylation signals. Optionally, the plasmid DNA of the present invention will also comprise a selection marker gene, such as that coding for antibiotic resistance. Marker genes of use in the present invention include but are not limited to neomycin, hygromycin-B, ampicillin, kanomycin, or puromycin.

For example, plasmids comprising the rat IL-10 sequence flanked by two AAV ITRs, a cytomegalovirus immediate early promoter enhancer, a chicken β-actin promoter, a polyadenylation signal, and a herpes simplex thymidine kinase promoter driving a neomycin resistance marker were used in some experiments demonstrating the usefulness of the present invention. In other experiments, plasmids comprising the human IL-10 sequence flanked by two AAV ITRs, a cytomegalovirus immediate early promoter enhancer, a cytomegalovirus immediate early promoter, a polyadenylation signal, and an ampicillin resistance marker were used. Details of these plasmids are disclosed in Milligan, et al., Pain 126:294-308 (2006).

Alternatively, the vector may be a viral vector. In general, the five most commonly used classes of viral systems used in gene therapy can be categorized into two groups according to whether their genomes integrate into host cellular chromatin (oncoretroviruses and lentiviruses) or persist in the cell nucleus predominantly as extrachromosomal episomes (adeno-associated virus, adenoviruses, herpesviruses, and integration-deficient lentiviruses). For example, in one embodiment of the present invention, viruses from the Parvoviridae family are utilized. The Parvoviridae is a family of small single-stranded, non-enveloped DNA viruses with genomes approximately 5000 nucleotides long. Included among the family members is adeno-associated virus (AAV), a dependent parvovirus that by definition requires co-infection with another virus (typically an adenovirus or herpesvirus) to initiate and sustain a productive infectious cycle. In the absence of such a helper virus, AAV is still competent to infect or transduce a target cell by receptor-mediated binding and internalization, penetrating the nucleus in both non-dividing and dividing cells.

Another viral delivery system useful with the IL-10 expression constructs of the present invention is a system based on viruses from the family Retroviridae. Retroviruses comprise single-stranded RNA animal viruses that are characterized by two unique features. First, the genome of a retrovirus is diploid, consisting of two copies of the RNA. Second, this RNA is transcribed by the virion-associated enzyme reverse transcriptase into double-stranded DNA. This double-stranded DNA or provirus can then integrate into the host genome and be passed from parent cell to progeny cells as a stably-integrated component of the host genome.

In some embodiments, lentiviruses are the preferred members of the retrovirus family for use in the present invention. Lentivirus vectors are often pseudotyped with vesicular stomatitis virus glycoprotein (VSV-G), and have been derived from the human immunodeficiency virus (HIV), the etiologic agent of the human acquired immunodeficiency syndrome (AIDS); visan-maedi, which causes encephalitis (visna) or pneumonia in sheep; equine infectious anemia virus (EIAV), which causes autoimmune hemolytic anemia and encephalopathy in horses; feline immunodeficiency virus (FIV), which causes immune deficiency in cats; bovine immunodeficiency virus (BIV) which causes lymphadenopathy and lymphocytosis in cattle; and simian immunodeficiency virus (SIV), which causes immune deficiency and encephalopathy in non-human primates. Vectors that are based on HIV generally retain <5% of the parental genome, and <25% of the genome is incorporated into packaging constructs, which minimizes the possibility of the generation of reverting replication-competent HIV. Biosafety has been further increased by the development of self-inactivating vectors that contain deletions of the regulatory elements in the downstream long-terminal-repeat sequence, eliminating transcription of the packaging signal that is required for vector mobilization. The main advantage to the use of lentiviral vectors is that gene transfer is persistent in most tissues or cell types due to integration of the viral vector. However, lentivirus that is integrase deficient could also be used.

Adenoviruses (Ads) are a relatively well characterized homogenous group of viruses, including over 50 serotypes. See, e.g., International PCT Application No. WO 95/27071. Adenoviruses are medium-sized (90-100 nm), nonenveloped (without an outer lipid bilayer) icosahedral viruses composed of a nucleocapsid and a double-stranded linear DNA genome. There are 57 described serotypes in humans, which are responsible for 5-10% of upper respiratory infections in children, and many infections in adults as well. They are classified as group I under the Baltimore classification scheme, meaning their genomes consist of double-stranded DNA, and are the largest nonenveloped viruses. Because of their large size, they are able to be transported through the endosome (i.e., envelope fusion is not necessary). The virion also has a unique "spike" or fiber associated with each penton base of the capsid that aids in attachment to the host cell via the coxsackie-adenovirus receptor on the surface of the host cell.

The adenovirus genome is linear, non-segmented double-stranded (ds) DNA that is between 26 and 45 kb, allowing the virus to theoretically carry 22 to 40 genes. Although this is significantly larger than other viruses in its Baltimore group, it is still a very simple virus and is heavily reliant on the host cell for survival and replication. Once the virus has successfully gained entry into the host cell, the endosome acidifies, which alters virus topology by causing capsid components to disassociate. With the help of cellular microtubules, the virus is transported to the nuclear pore complex, where the adenovirus particle disassembles. Viral DNA is subsequently released, which can enter the nucleus via the nuclear pore. After this the DNA associates with histone molecules. Thus, viral gene expression can occur and new virus particles can be generated.

Unlike most lentiviral vectors (i.e., those that can integrate, e.g., are not integrase deficient), adenoviral DNA does not integrate into the genome and is not replicated during cell division. The primary applications for adenovirus are in gene therapy and vaccination. Recombinant adenovirus-derived vectors, particularly those that reduce the potential for recombination and generation of wild-type virus, have also been constructed. See, International PCT Application Nos. WO 95/00655 and WO 95/11984.

Other viral or non-viral systems known to those skilled in the art also may be used to deliver IL-10 expression constructs of the present invention to the joint, including but not limited to gene-deleted adenovirus-transposon vectors that stably maintain virus-encoded transgenes in vivo through integration into host cells (see Yant, et al., Nature Biotech. 20:999-1004 (2002)); systems derived from Sindbis virus or Semliki forest virus (see Perri, et al., J. Virol. 74(20):9802-07 (2002)); systems derived from Newcastle disease virus or Sendai virus; or mini-circle DNA vectors devoid of bacterial DNA sequences (see Chen, et al., Molecular Therapy. 8(3): 495-500 (2003)). Mini-circle DNA as described in U.S. Patent Publication No. 2004/0214329 discloses vectors that provide for persistently high levels of nucleic acid transcription.

Once the IL-10 expression construct has been constructed, amplified and isolated by techniques known in the art, the IL-10 expression construct is then optionally, in some embodiments, encapsulated within microparticles. Techniques for encapsulating IL-10 expression construct vary depending on the type of microparticles used and such techniques are described in more detail infra. The microparticles of the present invention may be comprised of any biodegradable polymer. To be used successfully as a biodegradable polymer in the controlled drug delivery formulations of the present invention, the material must be chemically inert and free of leachable impurities. Ideally the polymer also has an appropriate physical structure, with minimal undesired aging, and is readily processable. Some of the materials include poly(2-hydroxy ethyl methacrylate), poly(N-vinyl pyrrolidone), poly(methyl methacrylate), poly (vinyl alcohol), poly(acrylic acid), polyacrylamide, poly (ethylene-co-vinyl acetate), poly(ethylene glycol), and poly (methacrylic acid). Biodegradable polymers of particular use in the present invention include polylactides (PLA), polyglycolides (PGA), poly(lactide-co-glycolides) (PLGA), polyanhydrides, polycaprolactone, poly-3-hydroxybutyrate and polyorthoesters. Such biodegradable polymers have been characterized extensively and can be formulated to exhibit desired degradation properties as is known in the art (see, e.g., Edlund & Albertsson, *Degradable Aliphatic Polyesters*, pp. 67-112 (2002), Barman, et al., J. of Controlled Release, 69:337-344 (2000); Cohen, et al., Pharmaceutical Res., (8): 713-720 (1991)).

In one particular embodiment of the invention, the polymer comprises poly(lactide-co-glycolides) (PLGA). PLGA is a copolymer which is used in a host of FDA approved therapeutic devices, owing to its biodegradability and biocompatibility. PLGA is synthesized by means of random ring-opening co-polymerization of two different monomers, the cyclic dimers (1,4-dioxane-2,5-diones) of glycolic acid and lactic acid. Common catalysts used in the preparation of this polymer include tin(II) 2-ethylhexanoate, tin(II) alkoxides, or aluminum isopropoxide. During polymerization, successive monomeric units of glycolic or lactic acid are linked together in PLGA by ester linkages, thus yielding a linear, aliphatic polyester as a product.

Depending on the ratio of lactide to glycolide used for the polymerization, different forms of PLGA can be obtained: these are usually identified in regard to the monomers' ratio used (e.g., PLGA 75:25 identifies a copolymer whose composition is 75% (molar percent) lactic acid and 25% (molar percent) glycolic acid). PLGA degrades by hydrolysis of its ester linkages in the presence of water. It has been shown that the time required for degradation of PLGA is related to the monomers' ratio used in production: the higher the content of glycolide units, the lower the time required for degradation. An exception to this rule is the copolymer with 50:50 monomers' ratio which exhibits the faster degradation (about two months). In addition, polymers that are end-capped with esters (as opposed to the free carboxylic acid) demonstrate longer degradation half-lives. Of particular use in the present invention is PLGA having a composition of between 20% and 80% lactic acid and between 80% and 20% glycolic acid. More preferred for use in the present invention is PLGA having a composition of between 65% and 35% lactic acid and between 35% and 65% glycolic acid. In one aspect of the present invention, PLGA having a composition of 50% lactic acid and 50% glycolic acid is used.

Additionally, the IL-10 expression constructs (pDNA) may be encapsulated in batches of microparticles having different release profiles; for example, 10% of the pDNA to be delivered may be encapsulated in microparticles having, e.g., a one day to four week release profile; 30% of the pDNA to be delivered may be encapsulated in microparticles having, e.g., a three week to six week release profile; 30% of the pDNA to be delivered may be encapsulated in microparticles having, e.g., a six week to ten week release profile; and 30% of the pDNA to be delivered may be encapsulated in microparticles having, e.g., an eight week to twelve week release profile. In such an embodiment, a single type of biodegradable polymer may be used, but used in formulations with different release profiles; alternatively, different biodegradable polymers having different release characteristics may be used. In yet another embodiment, the formulation of the microparticles may be varied so as to change the surface of the microparticles to enhance or retard, as desired, the travel of the therapeutic composition through, e.g., the synovial fluid of the joint.

Once microparticles are obtained, they are suspended in an acceptable diluent to form a therapeutic composition for administration to a subject. Similarly, if the IL-10 expression constructs of the present invention are delivered as naked DNA as opposed to being encapsulated, diluents are also used for administration to the subject. Such diluents (or excipients) include any pharmaceutical agent that does not itself induce the production of antibodies harmful to the individual receiving the composition, and that may be administered without undue toxicity. Pharmaceutically acceptable diluents may comprise sorbitol, alum, dextran, sulfate, large polymeric anions, any of the various TWEEN compounds, and liquids such as water, saline, glycerol or ethanol, oil and water emulsions, or adjuvants such as Freund's adjuvant. Pharmaceutically acceptable salts can be included therein as well, for example, mineral acid salts such as hydrochlorides, hydrobromides, phosphates, sulfates, and the like; and the salts of organic acids such as acetates, propionates, malonates, benzoates, and the like. Additionally, auxiliary substances, such as wetting or emulsifying agents, pH buffering substances, and the like may be present in such vehicles. In one aspect of the invention, different diluents are used based on their ability to migrate through the targeted site in joint. For example, for delivery in an adult human, diluents may be preferred that favor more rapid spread of the therapeutic composition through the joint; conversely, in children or small animals where the size of the joint is less of a concern, a diluent may be used that does not disperse the therapeutic composition quickly. A thorough discussion of pharmaceutically acceptable diluents/excipients is available in *Remington: The Science and Practice of Pharmacy*, 21$^{st}$ ed., Lippincott Williams & Wilkins (2005). Preferred diluents include but are not limited to Physiosol®, artificial synovial fluid, preservative-free 0.9% NaCl, lactated Ringer's injection solution, and Elliotts B® Solution.

Synthesizing and administering the compositions to be used in the methods of the present invention involve a series of steps. First, a plasmid is constructed comprising the various components described supra. Then the plasmid DNA (pDNA) is amplified and isolated by techniques well known in the art. Once the pDNA is isolated, it may be combined with polymers to form pDNA-containing microparticles. Methods for microparticle formation vary depending on the polymers used, however, a double emulsion technique is typically employed. First, a polymer is dissolved in an organic solvent. Next, pDNA is suspended in an aqueous solution and is added to the polymer solution. The two solutions are then mixed to form a first emulsion. The solutions can be mixed by vortexing or shaking or by passage through a particulate medium producing turbulence, or the mixture can be sonicated. Most preferable is any method by which the nucleic acid receives the least amount of damage in the form of nicking, shearing, or degradation, while still allowing the formation of an appropriate emulsion. During this process, the polymer forms into microparticles, many of which contain pDNA. If desired, one can isolate a small amount of the nucleic acid at this point in order to assess integrity, e.g., by gel electrophoresis.

The first emulsion is then added to an organic solution. The solution can be comprised of, for example, methylene chloride, ethyl acetate, or acetone, typically containing polyvinyl alcohol (PVA), and often having approximately a 1:100 ratio of the weight of PVA to the volume of the solution. The first emulsion is generally added to the organic solution with stirring in a homogenizer or sonicator. This process forms a second emulsion which is subsequently added to another organic solution with stirring (e.g., in a homogenizer). In one aspect of this method, the latter solution is 0.05% w/v PVA. The resultant microparticles are washed several times with water to remove the organic compounds. In some aspects of the present invention, more than approximately 40% of the resulting microparticles contain pDNA. In yet other aspects, more than approximately 50% of the resulting microparticles contain pDNA, in yet other aspects of the present invention, more than 55% of the resultant microparticles contain pDNA.

The ability to internalize differently-sized microparticles varies with cell type. In certain embodiments of the invention, macrophages and antigen-presenting cells were targeted. Such cells more efficiently internalize microparticles of less than about 5μ (see Shakweh, et al., Eur J of Pharmaceutics and Biopharmaceutics 61(1-2):1-13 (2005)). Thus, if desired, particles may be passed through sizing screens to selectively remove those larger than the desired size. In one particular aspect of the invention, microparticles of less than 5µ are used in the therapeutic composition, and in other particular aspects of the invention, microparticles of less than 3µ are used in the therapeutic composition. After washing, the particles can either be used immediately or be lyophilized for storage. The size distribution of the microparticles prepared by the methods described herein can be determined with, e.g., a Coulter™ counter or laser diffraction. Alternatively, the average size of the particles can be determined by visualization under a microscope fitted with a sizing slide or eyepiece. Alternatively, a scanning electron microscope can be used to assess both size and microparticle morphology.

Once IL-10 expression construct-containing microparticles are obtained, the microparticles can be suspended immediately in diluent or lyophilized for storage. The combination of the microparticles and diluent forms the therapeutic microparticle composition that can be administered by injection into a joint to an animal subject. The recombinant vectors can be introduced either in vivo or in vitro (also termed ex vivo) to treat joint inflammation. If transduced in vitro, the desired recipient cell or synovial fluid is removed from the subject, treated with pDNA-containing microparticles and reintroduced into the subject. Alternatively, syngeneic or xenogeneic cells can be transformed for delivery where such cells typically do not generate an inappropriate immune response in the subject. If administered in vivo, recombinant vectors or cells transformed with the vectors in vitro are delivered directly by injection into the joint.

The IL-10 expression constructs of the present invention are, in an alternative embodiment, administered as naked DNA. In such an embodiment, the IL-10 expression constructs are amplified, e.g., using good quality manufacturing practices. GMPs are enforced in the United States by the U.S. Food and Drug Administration (FDA), under Section 501(B) of the 1938 Food, Drug, and Cosmetic Act (21 USCS § 351).

Adjuvants appropriate for the present invention include adjuvants that increase the uptake of the IL-10 expression constructs of the present invention; that is, adjuvants appropriate for the present invention include any biologically-compatible agent that neutralizes or obviates the issue of introducing negatively-charged DNA into cells with a negatively-charged membrane. Such adjuvants include sugars such as mannose, glucose and sucrose; calcium phosphate; dendrimers (repetitively branched molecules); liposomes (spherical vesicles comprising a lipid bilayer) including cationic liposomes; DEAE-dextran including DEAE-dextran polyethylenimine; oligodeoxynucleotides; and high molecular weight hyaluronic acid (>1 MDa), an anionic nonsulfated glycosaminoglycan.

One adjuvant of particular interest is D-mannose. D-mannose is a simple hexose sugar with a molecular weight of 180.2 and is known to: decrease inflammatory processes during wound healing (Kossi J, et al., Eur Surg Res, 31(1): 74-82 (1999), reduce oxidative bursts required during inflammation (Rest R F, et al., J Leukoc Biol, 43(2):158-164 (1988)), suppress adjuvant-induced arthritis in a rat model (Willenborg D O, et al., Immunol Cell Biol, 70(Pt 6):369-377 (1996)), inhibit LPS-induced IL-1β, TNF-α, decrease NF-kB/p65 critical for proinflammatory cytokine expression, and decrease leukocyte influx following intratracheal instillation of LPS, which is a model of sepsis-associated acute lung injury and respiratory distress syndrome (Xu X L, et al., Inflamm Res, 57(3):104-110 (2008); Xu X, et al., Eur J Pharmacol, 641(2-3):229-237 2010)). The MR is a transmembrane glycoprotein pattern recognition receptor involved in host defense of innate immunity by recognizing mannosylated ligands (for example, lysosomal hydrolases) that can include a variety of bacteria, yeasts and parasites expressing mannosylated molecules (see, e.g., Engering A J, et al., Adv Exp Med Biol, 417:183-187 (1997); Linehan S A, et al., Adv Exp Med Biol, 479:1-14 (2000); Stahl P D, et al., Curr Opin Immunol, 10(1):50-55 (1998)).

Because the therapeutic compositions of the invention do not significantly induce an immune response or dose tolerance in subjects, they can be administered as needed for therapeutic effect. That is, the therapeutic anti-inflammatory composition can be delivered approximately every 40 to 120 days (or as required) as needed for therapeutic effect for shorter-term therapy. However, when longer-term therapy is desired, the therapeutic composition can be delivered approximately every 40 to 120 days (or more or less) as needed for therapeutic effect for greater than one year; and if necessary, for the life of the subject. Dosage frequency depends on the dosage, the adjuvant used and the health of the subject.

Dosage ranges of the therapeutic compositions used in the methods of the present invention vary from subject to subject, depending on the species, age, and general condition of the subject, the severity of the condition being treated, joint site, and the particular IL-10 expression construct to be delivered, whether or not the IL-10 expression construct if encapsulated, mode of administration, and the like. Dosage ranges include a therapeutically effective dose per joint at about 1-1000 µg vector DNA, about 5-750 µg vector DNA, about 10-600 µg vector DNA, 20-500 µg vector DNA, 25-250 µg vector DNA, or 50-100 µg vector DNA.

The IL-10 expression constructs or microparticles containing the IL-10 expression constructs used in the methods of the present invention may be co-administered in a "cocktail" with other therapeutic agents useful in treating joint inflammation including glucocorticoids; methotrexate; hydroxychlolquine; sulfasalazine; lefunomide; anti-TNF agents such as etanercept, infliximab and adalimumab; abatacept; hyaluronic acid, particularly high molecular weight hyaluronic acid (>1 MDa) such as Hyalgan, Orthovisc, or Synvisc at a dose of, e.g., 0.5-2.5% (5 to 25 mg/mL) from 1 to 5 mL, so from 5 mg to 125 mg per joint; and nonsteroidal anti-inflammatory drugs (NSAIDs). Additionally, the IL-10 expression constructs or microparticles containing the IL-10 expression constructs used in the methods of the present invention may be co-administered with cells, such as mesenchymal stem cells or other stem cells, including stem cells bioengineered to express IL-10 expression constructs. Generally, any method known in the art can be used to monitor success of treatment in humans, including both clinical and phenotypic indicators.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Amplification and Purification of pDNA

The plasmid construct encoding for rat interleukin-10 (pDNA-IL-10F129S) has been previously described in detail in Milligan, et al., Pain 126(1-3): 294-308 (2006). In short, The plasmid consists of a 5.9 Kilobase (Kb) circular plasmid DNA containing a transcriptional cassette consisting of a cytomegalovirus enhancer/chicken beta-actin promoter (CMV enh/CB pro) driving expression of the rat IL-10 gene containing a point mutation (F129S) and a viral SV40 polyadenylation signal. The transcription cassette is flanked by a 149 bp inverted terminal repeat sequence. An identical plasmid lacking the IL-10 gene was used as a pDNA control. Both plasmids were amplified in SURE 2 Supercompetent E. coli cells (Agilent Technologies, USA) and isolated using an endotoxin free Giga plasmid purification kit (Qiagen, Valencia, Calif., USA) according to the manufacturer's instructions. Purified, endotoxin-free plasmids were resuspended in sterile Dulbecco's PBS (DPBS, 1, 0.1 micron pore-filtered, pH 7.2, catalog #14190-144; Gibco, Invitrogen Corp, Grand Island, N.Y., USA) with 3% sucrose (DPBS-3%). The DPBS-3% vehicle was prepared using molecular biology grade D (+)-sucrose (b-D-fructofuranosyl-a-D-glucopyranoside; Sigma-Aldrich, St. Louis, Mo., USA) in DPBS, 0.2 um sterile filtered (pyrogen-free syringe filter unit, catalog #25AS020AS, Life Science Products, Inc., CO, USA) and stored in sterile, 15 ml conical tubes at 4° C. until the time of use.

Microparticle Preparation and Characterization

Microparticles were prepared using a modified double emulsion/solvent evaporation protocol (A. M. Tinsley-Bown, et al., J. of Controlled Release 66(2-3): 229-41 (2006)). Briefly, a 50:50 PLGA copolymer (MW 75,000, Lactel Absorbable Polymers) was dissolved in ethyl acetate (Sigma). Vehicle alone (phosphate buffered saline (PBS)+ 3% (w/v) sucrose (Sigma)) or pDNA in vehicle were emulsified in the PLGA solution followed by a second emulsion in a 5% (w/v) polyvinyl alcohol, 28% calcium chloride, 3% sucrose (Sigma) and 7% (v/v) ethyl acetate solution. After 4 hours of hardening in a wash solution, the resulting microparticles were collected, lyophilized and stored at 4° C. Scanning electron microscopy (SEM) was used to examine microparticle morphology. The diameters of >1000 microparticles present in 10 different images were measured with NIH ImageJ software and binned particle diameters were used to generate a normalized frequency distribution. The zeta potential of the microparticles was measured with a Nicomp 380 ZLS Zeta Potential Analyzer, and the endotoxin levels of the resultant microparticles were tested by the LAL assay, using serial dilution as a control for inhibition. The microparticles utilized exhibited a spherical and smooth morphology under SEM and a zeta-potential of −28.04±2.12 mV. The microparticles exhibited a heterogeneous size distribution with an overall median diameter of 4.67±0.26 µm, which is consistent with similar methods of microparticle manufacturing and the pDNA encapsulation efficiency for the particles was 55.1%.

Total pDNA encapsulation was assessed by extracting pDNA from microparticles via sodium hydroxide dissolution, measuring the absorbance at 260 nm and comparing obtained values to DNA standards at known concentrations. Final pDNA loadings were 8.78±0.65 µg pDNA/mgPLGA for PLGA-pDNA-IL-10 microparticles. Aqueous extraction of pDNA was conducted by dissolving microparticles in chloroform and allowing the pDNA to migrate into aqueous buffer. The extracted pDNA was subsequently concentrated by precipitation with ethanol and re-suspended in PBS+3% sucrose vehicle. The structural integrity of the aqueous extracted pDNA was compared against unencapsulated pDNA (which was similarly exposed to the aqueous extraction process) by loading 2 µg of total pDNA into the wells of a 1.0% agarose gel containing ethidium bromide, running the gel at 75 V for 2 hours, and imaging the gel with UV trans-illumination at 305 nm. Biological activity of aqueous extracted pDNA was assessed by lipofectamine-mediated transfection into human embryonic kindey-293 cells according to manufacturer protocols (Invitrogen) and IL-10 protein concentrations in cell culture supernatants collected 24 hours after transfection with aqueous extracted and unencapsulated pDNA were assessed by ELISA (R&D Systems). In vitro release profiling was conducted by incubating microparticles in PBS over time in a water bath at 37° C. and pDNA contents in the supernatant were quantified by a PicoGreen assay (Milligan, et al., Neuron Glia Biology 2(4) 293-308 (2006)).

Agarose gel electrophoresis of aqueous extracted pDNA from microparticles compared to unencapsulated pDNA indicated that a significant amount of the relaxed and supercoiled pDNA structural integrity was preserved after encapsulation, although a slight detection of linearized pDNA and slight alterations in the migration of multimeric pDNA species were observed after encapsulation. By comparing resultant IL-10 protein expression levels in the supernatants of human embryonic kidney-293 cells 24 hours after lipofectamine-mediated transfection with dose-matched microparticle extracted or unencapsulated pDNA, it was determined that the microparticle extracted pDNA-IL-10 exhibited a 96.8% biological activity retention for the resultant production of IL-10 (data not shown). In vitro pDNA release analysis demonstrated that 30% of the pDNA was released after 3 days and steady release was achieved for greater than 75 days. This two-phase release profile is a common characteristic of macromolecule release from emulsion based PLGA microparticles, where the enhanced phase of initial pDNA release is due to an increased pDNA content on or near the surface of the microparticles which is followed by a sustained release and diffusion of pDNA from the microparticle interior (Yeo, Archive of Endotoxin Res. 27(1): 1-12 (2004)). Endotoxin levels from microparticles with and without encapsulated pDNA were below the limits of detection for the LAL assay up to a microparticle concentration of 10 mg/ml (1 mg of microparticles/well).

D-Mannose

In embodiments where an adjuvant such as D-Mannose is employed, D-mannose (catalog #M6020) can be purchased carrier free from Sigma-Aldrich (St. Louis, Mo.). The D-mannose is combined with 0.1% BSA in sterile saline, and administered via intr-articular injection either concurrently with the IL-10 expression construct or from one to ten day prior to administration of the IL-10 expression construct. D-mannose is typically delivered at a dosage of 2.5 µg-500 µg per joint in canines.

Administration for Treatment of Joint Inflammation in Canines

The IL-10 expression construct (pDNA-IL-10$^{F129S}$) as "naked" pDNA was administered by acute intra-articular injection to an affected joint in a series of canines. Under IV sedation and anesthetic monitoring, the canine patient's affected joint was surgically clipped to remove all fur over the affected joint and sterilized utilizing a surgical scrub, such as chlorahexidine 2%. The patient's heart rate, blood pressure, oxygen saturation, ventilation and heart rhythm was continuously monitored. A 22- or 20-gauge hypodermic needle was inserted into the synovial space. Synovial fluid was aspirated prior to administration of the pDNA to assure proper placement of the needle. The syringe containing synovial fluid aspirate was replaced while maintaining intra-articular needle placement. Once the synovial fluid was aspirated, the therapeutic anti-inflammatory composition was administered into the joint utilizing the same intra-articular needle. Up to 1 mg plasmid DNA equivalent was injected, although as little as 700 µg was found to be effective. Where the volume per joint injection during administration did exceed 1 ml, joint fluid was aspirated to compensate. Following the successful placement of the therapeutic anti-inflammatory composition within the joint space, the patient was reversed from the sedative affects and clinically monitored. Any changes to blood pressure, heart rate, oxygenation, ventilation or heart rhythm during the procedure was corrected with the proper medical treatments. Anticipated effects of sedation include bradycardia, hypotension, hypoventilation. Oxygen therapy was continuous throughout the entire procedure to maximize oxygen saturation levels. Sedative medications tailoring to individual patient and sole medications or combinations of the following:

A: Dexmedetomidine 0.5 mg/m$^2$, Reversal (atipamazole 0.05-0.2 mg/lb)
B: Opioids—Butorphanol (0.05-0.1 mg/lb),
C: Propofol—i.v. to effect
D: Benzodiazepines (diazepam): 0.1-0.2 mg/lb Subjects remained at the veterinary facility for the day (less than 12 hours) and then were allowed go home.

Clinical assessments included owner Canine Brief Pain Inventory behavioral assessments, veterinarian clinical Visual Analog Scale for pain and mobility, goniometry, pharmaceutical reduction/dependency, and video and gait monitoring. FIG. 1 shows results in the form of bar graphs illustrating clinical assessment of the functional improvement and pain reduction achieved treating osteoarthritis of forelimb joints in canines after administration of the therapeutic IL-10 expression constructs of the present invention. Note that administration of the IL-10 expression constructs of the present invention resulted in significant functional improvement and pain reduction, in all of walk, trot, manipulation, range of motion and functional disability, particularly at the 11-week mark.

Figure 2:
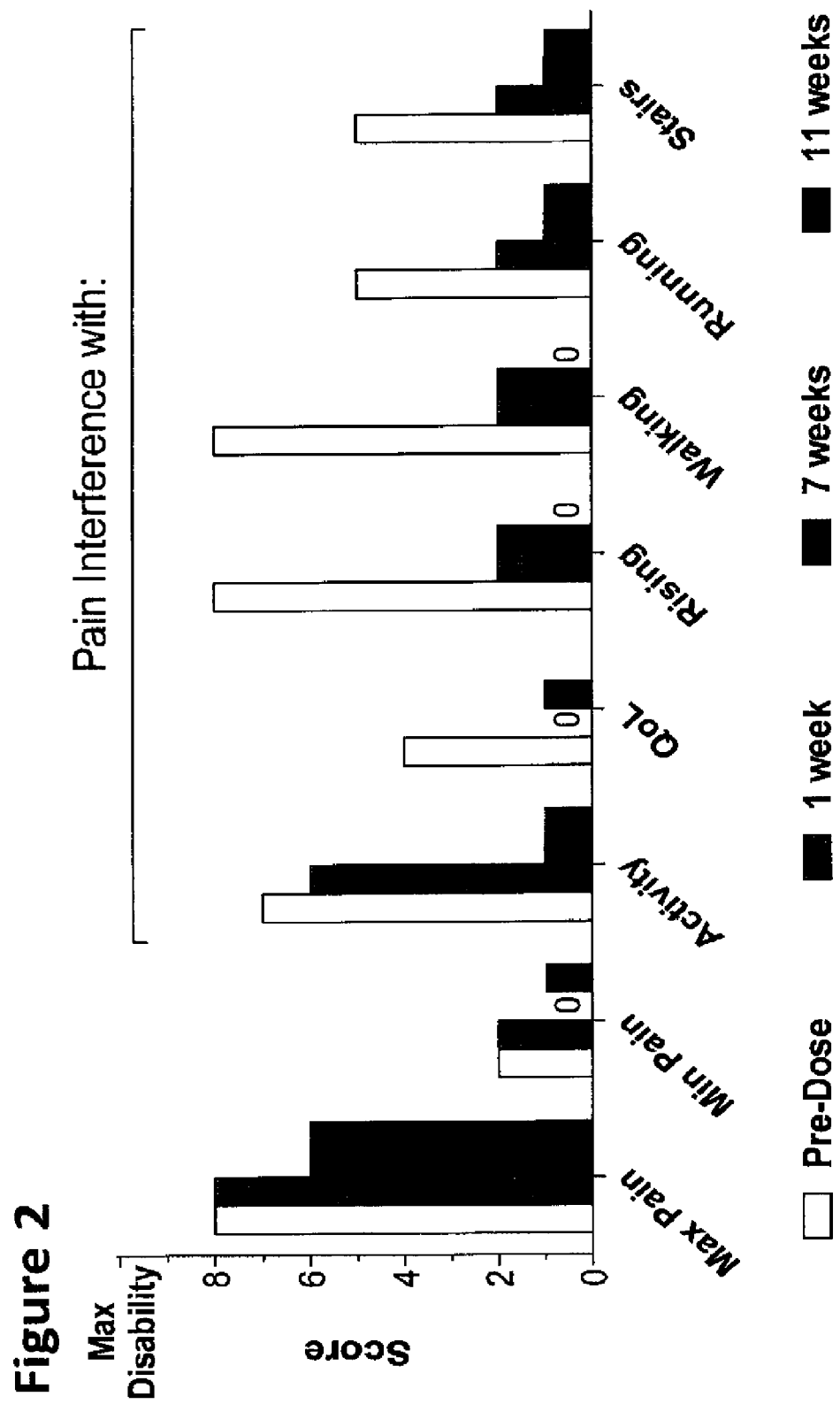
FIG. 2 shows results in the form of bar graphs illustrating owner assessment of the functional improvement and pain reduction achieved treating osteoarthritis of forelimb joints in canines after administration of the therapeutic IL-10 expression constructs of the present invention.

FIG. 2 shows results in the form of bar graphs illustrating owner assessment of the functional improvement and pain reduction achieved treating osteoarthritis of forelimb joints in canines after administration of the therapeutic IL-10 expression constructs of the present invention. Note that again, there was significant improvement in all parameters of activity, quality of life, rising, walking, running and climbing stairs even at 1 week.

Figure 3:
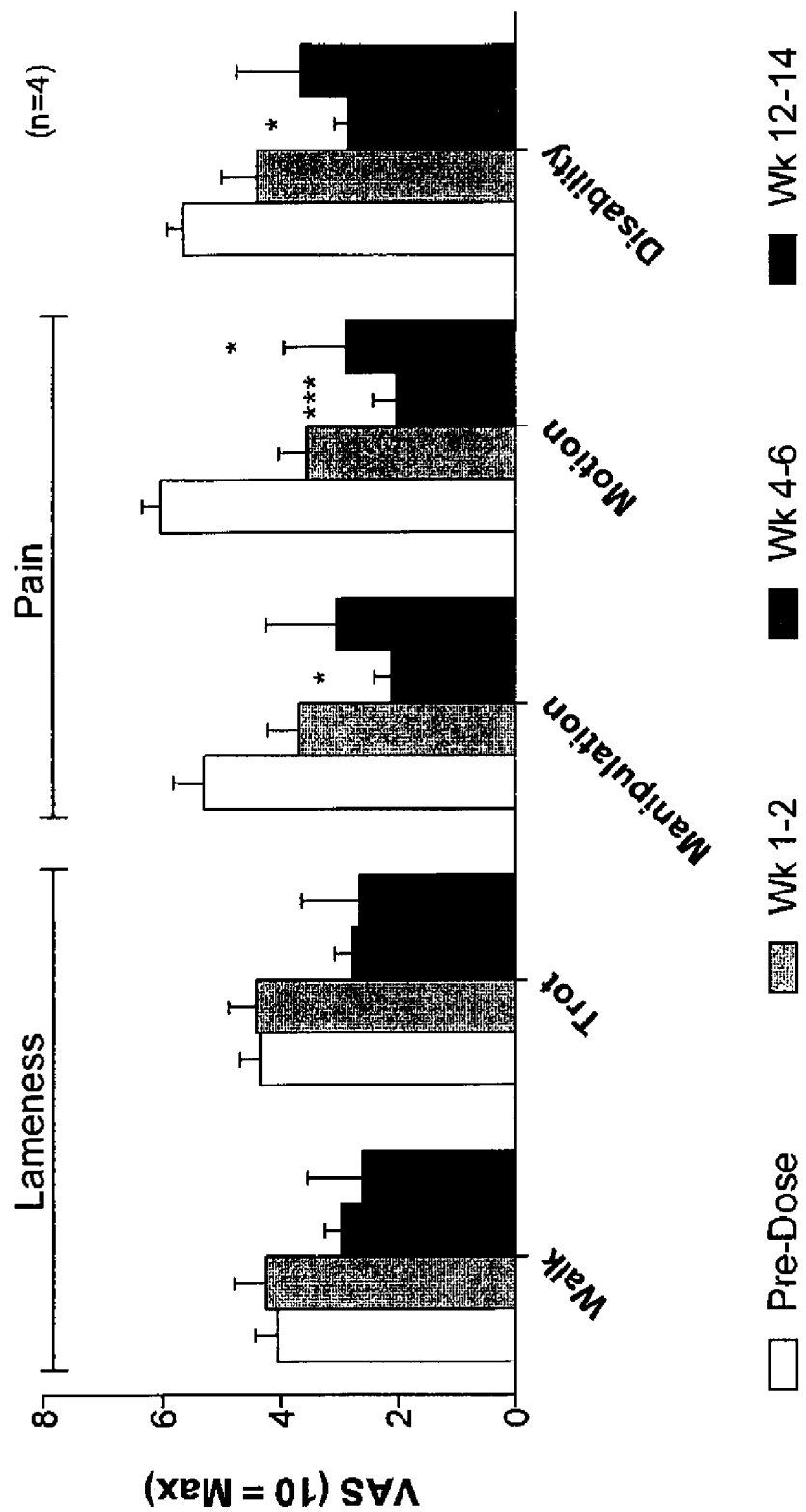
FIG. 3 shows results in the form of bar graphs illustrating clinical assessment of the functional improvement and pain reduction achieved treating osteoarthritis of forelimb joints in canines after administration of the therapeutic IL-10 expression constructs of the present invention (pooled data).

FIG. 3 shows results in the form of bar graphs illustrating clinical assessment of the functional improvement and pain reduction achieved treating osteoarthritis of forelimb joints in canines after administration of the therapeutic IL-10 expression constructs of the present invention (pooled data). The results of clinical assessment show significant positive results, particularly in pain.

Figure 4:
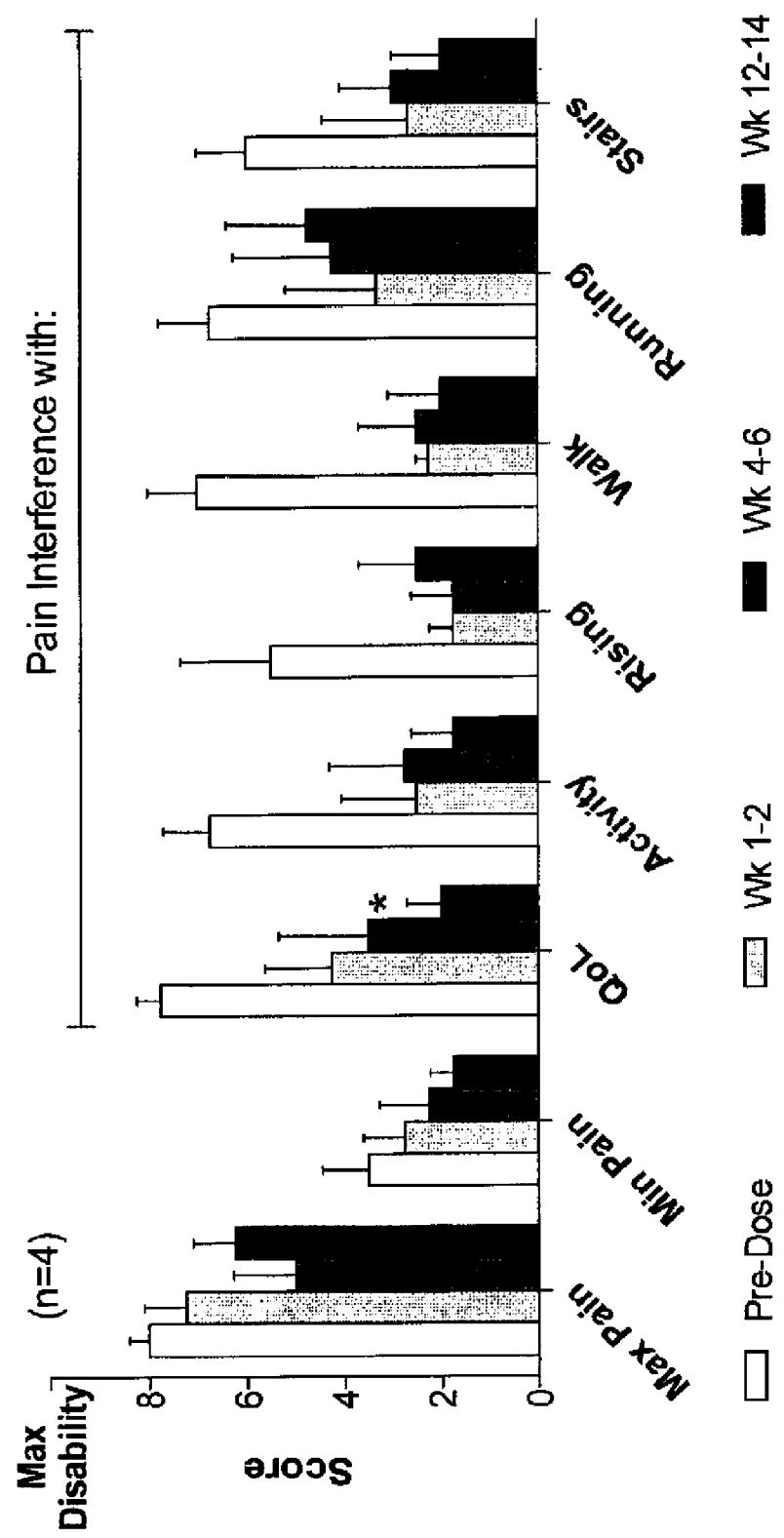
FIG. 4 shows results in the form of bar graphs illustrating owner assessment of the functional improvement and pain reduction achieved treating osteoarthritis of forelimb joints in canines after administration of the therapeutic IL-10 expression constructs of the present invention (pooled data).

FIG. 4 shows results in the form of bar graphs illustrating owner assessment of the functional improvement and pain reduction achieved treating osteoarthritis of forelimb joints in canines after administration of the therapeutic IL-10 expression constructs of the present invention (pooled data). Note in these results, similar to the results in FIG. 2, there was significant improvement in all parameters of activity, quality of life, rising, walking, running and climbing stairs even at 1 week.

Figure 5:
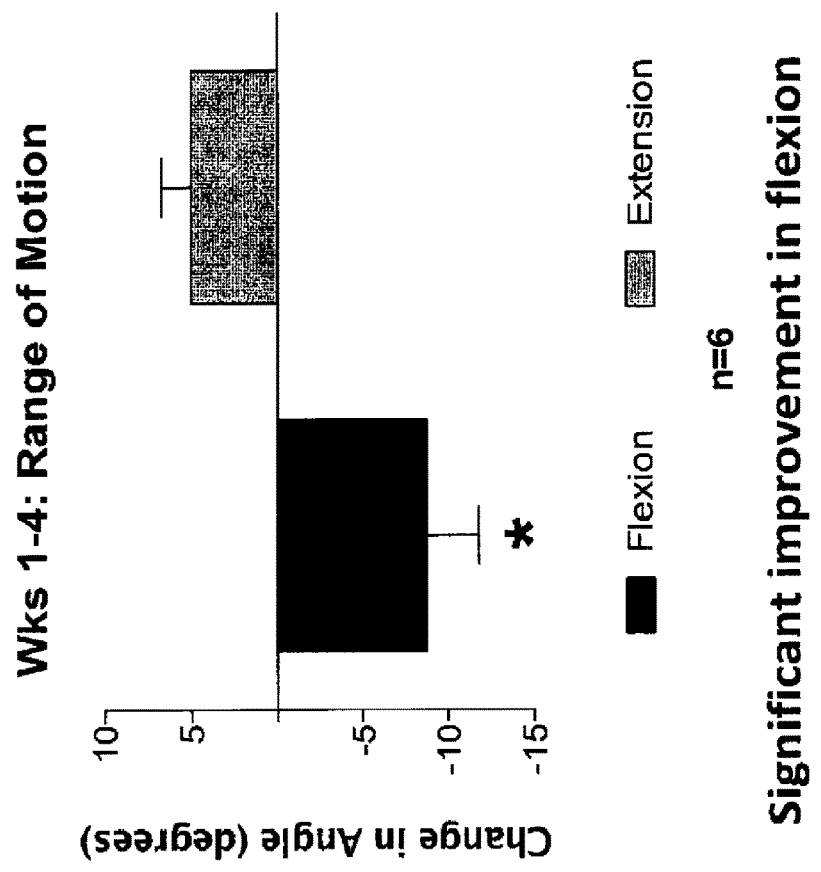
FIG. 5 shows results illustrating improvements in range of motion achieved treating osteoarthritis of forelimb joints in canines after administration of the therapeutic IL-10 expression constructs of the present invention (pooled data).

FIG. 5 shows results illustrating improvements in range of motion achieved treating osteoarthritis of forelimb joints in canines after administration of the therapeutic IL-10 expression constructs of the present invention (pooled data). Note that the change in angle degrees showed significant improvement.

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

We claim:

1. A method for treating inflammatory joint disease in a mammalian subject, said method comprising injecting into the inflamed joint not more frequently than every 60 days a therapeutic anti-inflammatory composition comprising 25 µg to 750 µg of a DNA IL-10$^{F129S}$ expression construct formulated in poly(lactic-co-glycolic acid) microparticles, wherein the IL-10$^{F129S}$ expression construct comprises a plasmid backbone, a nucleic acid sequence encoding interleukin-10$^{F129S}$, adeno-associated virus (AAV) inverted terminal repeat (ITR) sequences flanking the nucleic acid sequence encoding interleukin 10$^{F129S}$, one or more promoter sequences, and a polyadenylation signal operably linked to the nucleic acid sequence encoding interleukin 10$^{F129S}$, and a marker gene.

2. The method of claim 1, wherein the therapeutic anti-inflammatory composition is administered with an adjuvant.

3. The method of claim 2, wherein the adjuvant is selected from D-mannose, sucrose, glucose, calcium phosphate, a dendrimer, an oligonucleotide, high molecular weight hyaluronic acid, and a lipid.

4. The method of claim 1, wherein the composition further comprises a diluent.

5. The method of claim 1, wherein the joint is a knee, elbow, wrist, ankle, hip, shoulder, or spine.

6. The method of claim 1, wherein the inflammatory joint disease is arthritis, tendonitis, bursitis, inflammation of the ligament, synovitis, gout, or systemic lupus erythematosus.

7. The method of claim 1, wherein the poly(lactic-co-glycolic acid) comprises 50:50 poly(lactic-co-glycolic acid).

8. The method of claim 1, wherein the IL-10 expression construct further comprises one or more control sequences operably linked to the nucleic acid sequence encoding interleukin $10^{F129S}$ independently selected from the group consisting of transcription termination sequences, upstream regulatory domains, and internal ribosome entry sites.

9. The method of claim 1, wherein the one or more promoter sequences is independently selected from the group consisting of chicken or human β-actin promoters, cytomegalovirus immediate early promoters, glyceraldehydd 3-phosphate dehydrogenase (GADPH) promoters, elongation factor 1 α (eF1 α) promoters, GFAP promoters, murine leukemia virus (MLV) promoters, herpes simplex virus thymidine kinase (TK) promoters, and woodchuck hepatitis virus post-transcriptional regulatory element (WPRE) promoters.

10. The method of claim 1, wherein the polyadenylation signal is independently selected from the group consisting of SV40 polyadenylation signal, bovine growth hormone polyadenylation signal, and synthetic polyadenylation signals.

11. The method of claim 1, wherein the construct comprises:
two AAV ITRs;
a chicken β-actin promoter, herpes simplex virus thymidine kinase (TK) promoter, SV40 polyadenylation signal, and cytomegalovirus immediate early promoter enhancer; and
a neomycin resistance marker.

12. The method of claim 1, wherein the construct comprises:
two AAV ITRs;
a cytomegalovirus immediate early promoter, SV40 polyadenylation signal, and cytomegalovirus immediate early promoter enhancer; and
an ampicillin resistance marker.

13. The method of claim 1, wherein the construct comprises:
two AAV ITRs;
a cytomegalovirus immediate early promoter, SV40 polyadenylation signal, and cytomegalovirus immediate early promoter enhancer; and
a kanamycin resistance marker.

14. A method for treating inflammatory joint disease in a mammalian subject, said method comprising injecting into the inflamed joint not more frequently than every 60 days a therapeutic anti-inflammatory composition comprising 25 μg to 750 μg of a DNA IL-$10^{F129S}$ expression construct administered with an adjuvant, wherein the adjuvant comprises a sugar, wherein the IL-$10^{F129S}$ expression construct comprises a plasmid backbone, a nucleic acid sequence encoding interleukin-$10^{F129S}$, adeno-associated virus (AAV) inverted terminal repeat (ITR) sequences flanking the nucleic acid sequence encoding interleukin $10^{F129S}$, one or more promoter sequences, and a polyadenylation signal operably linked to the nucleic acid sequence encoding interleukin $10^{F129S}$, and a marker gene.

15. The method of claim 14, wherein the adjuvant is selected from D-mannose, sucrose, and glucose.

16. The method of claim 14, wherein the composition further comprises a diluent.

17. The method of claim 14, wherein the joint is a knee, elbow, wrist, ankle, hip, shoulder, or spine.

18. The method of claim 14, wherein the inflammatory joint disease is arthritis, tendonitis, bursitis, inflammation of the ligament, synovitis, gout, or systemic lupus erythematosus.

19. The method of claim 14, wherein the IL-$10^{F129S}$ expression construct further comprises one or more control sequences operably linked to the nucleic acid sequence encoding interleukin $10^{F129S}$ independently selected from the group consisting of transcription termination sequences, upstream regulatory domains, and internal ribosome entry sites.

20. The method of claim 14, wherein the one or more promoter sequences is independently selected from the group consisting of chicken or human β-actin promoters, cytomegalovirus immediate early promoters, glyceraldehyde 3-phosphate dehydrogenase (GADPH) promoters, elongation factor 1 α (eF1 α) promoters, GFAP promoters, murine leukemia virus (MLV) promoters, herpes simplex virus thymidine kinase (TK) promoters, and woodchuck hepatitis virus post-transcriptional regulatory element (WPRE) promoters.

21. The method of claim 14, wherein the polyadenylation signal is independently selected from the group consisting of SV40 polyadenylation signal, bovine growth hormone polyadenylation signal, and synthetic polyadenylation signals.

22. The method of claim 14, wherein the construct comprises:
two AAV ITRs;
a chicken β-actin promoter, herpes simplex virus thymidine kinase (TK) promoter, SV40 polyadenylation signal, and cytomegalovirus immediate early promoter enhancer; and
a neomycin resistance marker.

23. The method of claim 14, wherein the construct comprises:
two AAV ITRs;
a cytomegalovirus immediate early promoter, SV40 polyadenylation signal, and cytomegalovirus immediate early promoter enhancer; and
an ampicillin resistance marker.

24. The method of claim 14, wherein the construct comprises:
two AAV ITRs;
a cytomegalovirus immediate early promoter, SV40 polyadenylation signal, and cytomegalovirus immediate early promoter enhancer; and
a kanamycin resistance marker.

25. The method of claim 6, wherein the arthritis is rheumatoid arthritis.

26. The method of claim 6, wherein the arthritis is osteoarthritis.

27. The method of claim 1, wherein the method comprises injecting into the inflamed joint not more frequently than every 90 days.

28. The method of claim 1, wherein the method comprises injecting into the inflamed joint not more frequently than every 120 days.

29. The method of claim 1, wherein the composition comprises 50 μg to 500 μg of a DNA IL-$10^{F129}$ expression construct.

30. The method of claim 1, wherein the composition comprises 50 μg to 250 μg of a DNA IL-$10^{F129}$ expression construct.

31. The method of claim 18, wherein the arthritis is rheumatoid arthritis.

32. The method of claim 18, wherein the arthritis is osteoarthritis.

33. The method of claim 14, wherein the method comprises injecting into the inflamed joint not more frequently than every 90 days.

34. The method of claim 14, wherein the method comprises injecting into the inflamed joint not more frequently than every 120 days.

35. The method of claim 14, wherein the composition comprises 50 μg to 500 μg of a DNA IL-10$^{F129}$ expression construct.

36. The method of claim 14, wherein the composition comprises 50 μg to 250 μg of a DNA IL-10$^{F129S}$ expression construct.

\* \* \* \* \*

UNITED STATES PATENT AND TRADEMARK OFFICE
CERTIFICATE OF CORRECTION

PATENT NO. : 10,512,672 B2
APPLICATION NO. : 14/905915
DATED : December 24, 2019
INVENTOR(S) : Raymond A. Chavez et al.

Page 1 of 2

It is certified that error appears in the above-identified patent and that said Letters Patent is hereby corrected as shown below:

On the Title Page

Item (71), please amend the Applicants section as shown below:
(71) Applicants: Xalud Therapeutics, Inc., Berkeley, CA (US); The Regents of the University of Colorado, a Body Corporate, Denver, CO (US)

Item (72), please amend the Inventors section as shown below:
(72) Inventors: Raymond A. Chavez, Alameda, CA (US); Linda R. Watkins, Boulder, CO (US); Robert Landry, Erie, CO (US)

In the Claims

In Claim 9, at Column 21, Lines 13-14, the text:
"glyceraldehydd 3-phosphate dehydrogenase (GADPH) promoters"
Should be replaced with the text:
--glyceraldehyde 3-phosphate dehydrogenase (GADPH) promoters--

In Claim 29, at Column 22, Lines 59-60, the text:
"DNA IL-10$^{F129}$ expression construct"
Should be replaced with the text:
--DNA IL-10$^{F129S}$ expression construct--

In Claim 30, at Column 22, Lines 62-63, the text:
"DNA IL-10$^{F129}$ expression construct"
Should be replaced with the text:
--DNA IL-10$^{F129S}$ expression construct--

In Claim 35, at Column 23, Lines 8-9, the text:
"DNA IL-10$^{F129}$ expression construct"

Signed and Sealed this
Twenty-seventh Day of October, 2020

Andrei Iancu
*Director of the United States Patent and Trademark Office*

Should be replaced with the text:
--DNA IL-10$^{F129S}$ expression construct--